US011266399B2

(12) United States Patent
Aravalli et al.

(10) Patent No.: US 11,266,399 B2
(45) Date of Patent: Mar. 8, 2022

(54) SURGICAL SUTURING INSTRUMENTS

(71) Applicant: Covidien LP, Mansfield, MA (US)

(72) Inventors: Avvln Srinivasa Murthy Aravalli, Tanuku (IN); Jaroslaw T Malkowski, Trumbull, CT (US); Henry E. Holsten, Hamden, CT (US)

(73) Assignee: Covidien LP, Mansfield, MA (US)

( * ) Notice: Subject to any disclaimer, the term of this patent is extended or adjusted under 35 U.S.C. 154(b) by 206 days.

(21) Appl. No.: 16/454,113

(22) Filed: Jun. 27, 2019

(65) Prior Publication Data

US 2019/0314011 A1 Oct. 17, 2019

Related U.S. Application Data

(63) Continuation-in-part of application No. 15/863,806, filed on Jan. 5, 2018, now Pat. No. 10,595,855.

(60) Provisional application No. 62/462,512, filed on Feb. 23, 2017.

(51) Int. Cl.
*A61B 17/04* (2006.01)
*A61B 17/06* (2006.01)

(52) U.S. Cl.
CPC ...... *A61B 17/0469* (2013.01); *A61B 17/0482* (2013.01); *A61B 17/06066* (2013.01); *A61B 2017/0474* (2013.01)

(58) Field of Classification Search
CPC ............ A61B 17/0469; A61B 17/0482; A61B 17/06066; A61B 17/3421; A61B 17/29; A61B 17/0625; A61B 34/30; A61B 34/37; A61B 2017/0474; A61B 2017/00367; A61B 2017/00876; A61B 2017/06047;

(Continued)

(56) References Cited

U.S. PATENT DOCUMENTS

| 4,027,608 | A | 6/1977 | Arbuckle |
| 5,437,681 | A | 8/1995 | Meade et al. |
| 5,674,229 | A | 10/1997 | Tovey et al. |

(Continued)

FOREIGN PATENT DOCUMENTS

| EP | 0552430 A1 | 7/1993 |
| EP | 3366227 A1 | 8/2018 |

(Continued)

OTHER PUBLICATIONS

European Search Report dated Jul. 24, 2018, corresponding to European Application No. 18158027.5; 5 pages.

(Continued)

*Primary Examiner* — Tan-Uyen T Ho
*Assistant Examiner* — Chima U Igboko

(57) ABSTRACT

A surgical suturing instrument includes first and second jaw members each defining a hole for detachable receipt of opposite ends of a curved needle. The first jaw member is rotatable relative to the second jaw member to move and transfer the curved needle between the jaw members. A first elongate locking element is slidable within the first jaw member between non-locking and locking positions. When the first elongate locking element is in the locking position and the curved needle is disposed within the hole of the first jaw member, a portion of the first elongate locking element is received in a notch defined in an end of the curved needle to selectively secure the curved needle to the first jaw member.

20 Claims, 21 Drawing Sheets

(58) Field of Classification Search
CPC .... A61B 2017/0608; A61B 2017/0609; A61B 2034/301
See application file for complete search history.

(56) References Cited

U.S. PATENT DOCUMENTS

| | | | |
|---|---|---|---|
| 5,707,379 | A | 1/1998 | Fleenor et al. |
| 5,820,631 | A | 10/1998 | Nobles |
| 5,954,733 | A | 9/1999 | Yoon |
| 5,993,466 | A | 11/1999 | Yoon |
| 6,126,665 | A | 10/2000 | Yoon |
| 6,454,777 | B1 | 9/2002 | Green |
| 7,033,370 | B2 | 4/2006 | Gordon et al. |
| 7,062,216 | B2 | 6/2006 | Nobe et al. |
| 7,587,166 | B2 | 9/2009 | Aono |
| 7,588,583 | B2 | 9/2009 | Hamilton et al. |
| 8,292,905 | B2 | 10/2012 | Taylor et al. |
| 8,702,732 | B2 | 4/2014 | Woodard, Jr. et al. |
| 2010/0010512 | A1* | 1/2010 | Taylor ................ A61B 17/0469 606/144 |
| 2013/0245643 | A1* | 9/2013 | Woodard, Jr. ..... A61B 17/0482 606/144 |
| 2013/0267969 | A1 | 10/2013 | Martin et al. |
| 2015/0272603 | A1 | 10/2015 | Shelton, IV et al. |

FOREIGN PATENT DOCUMENTS

| | | |
|---|---|---|
| JP | 2010505524 A | 2/2010 |
| JP | 2013529981 A | 7/2013 |

OTHER PUBLICATIONS

European Search Report dated Nov. 26, 2020, issued in corresponding EP Appln. No. 20182605, 8 pages.

Japanese Office Action dated Oct. 1, 2021, issued in corresponding Japanese Appln. No. 2018016954, 5 pages.

* cited by examiner

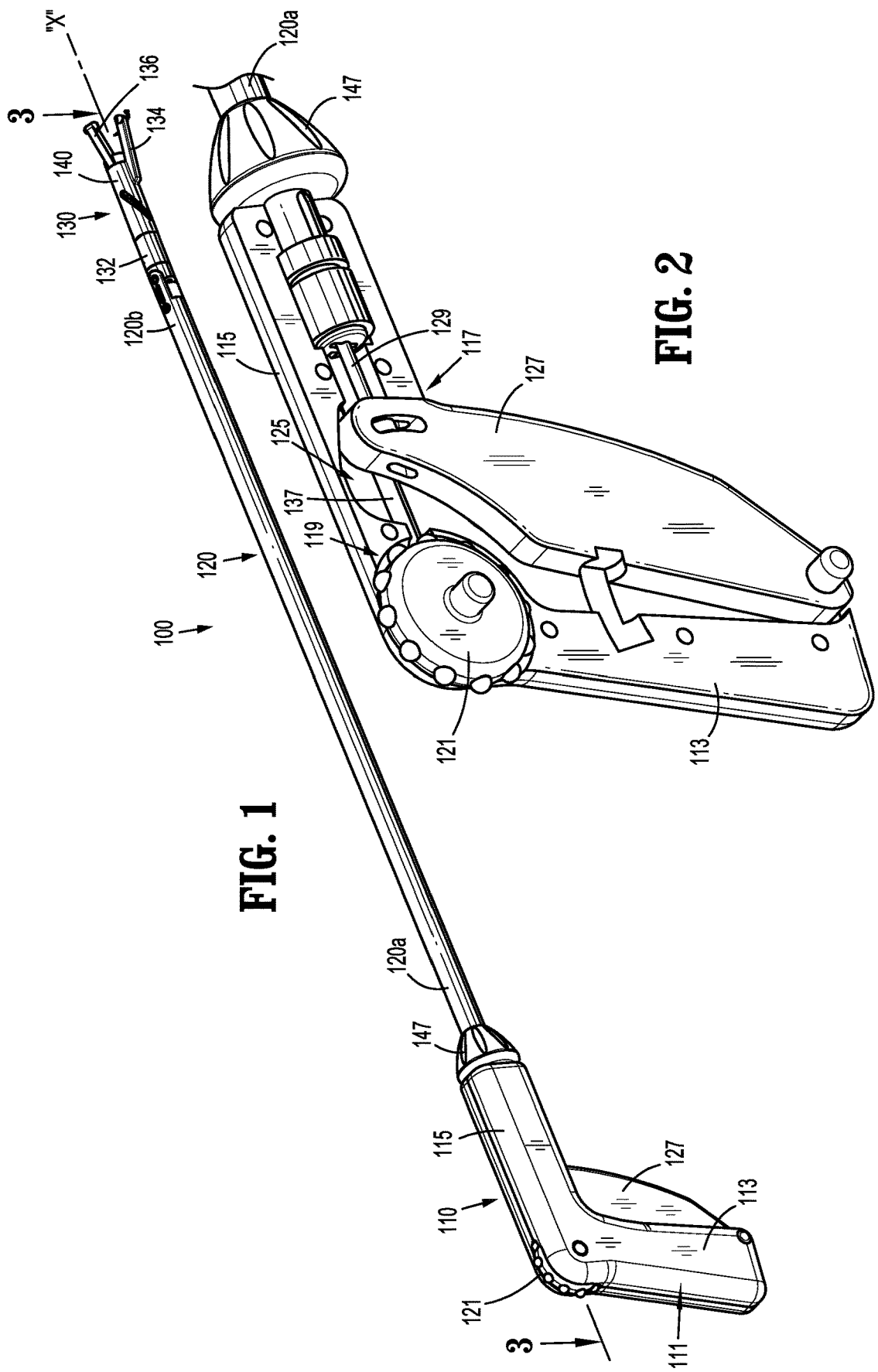

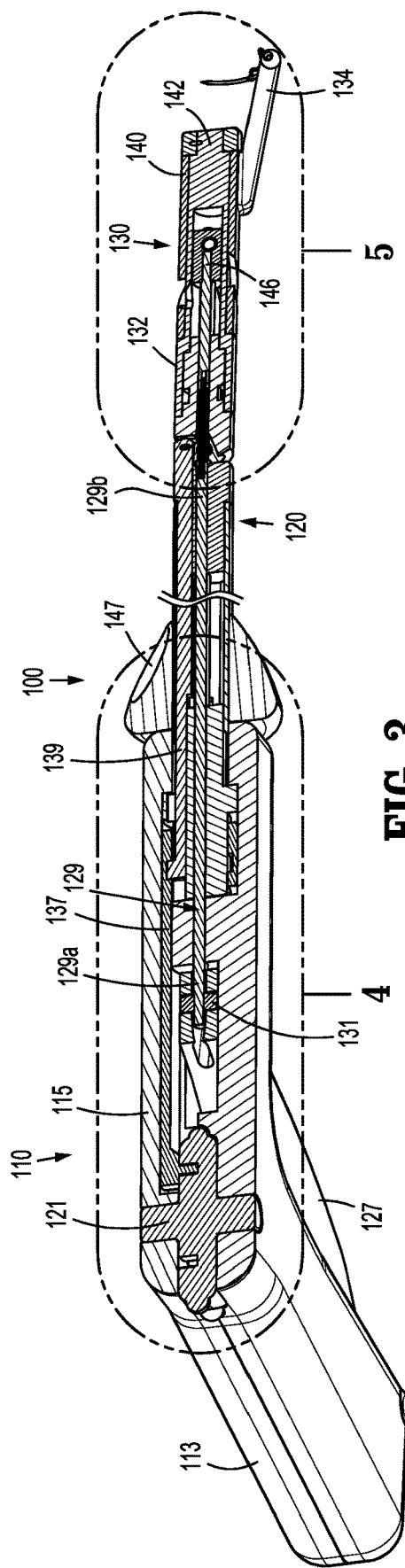
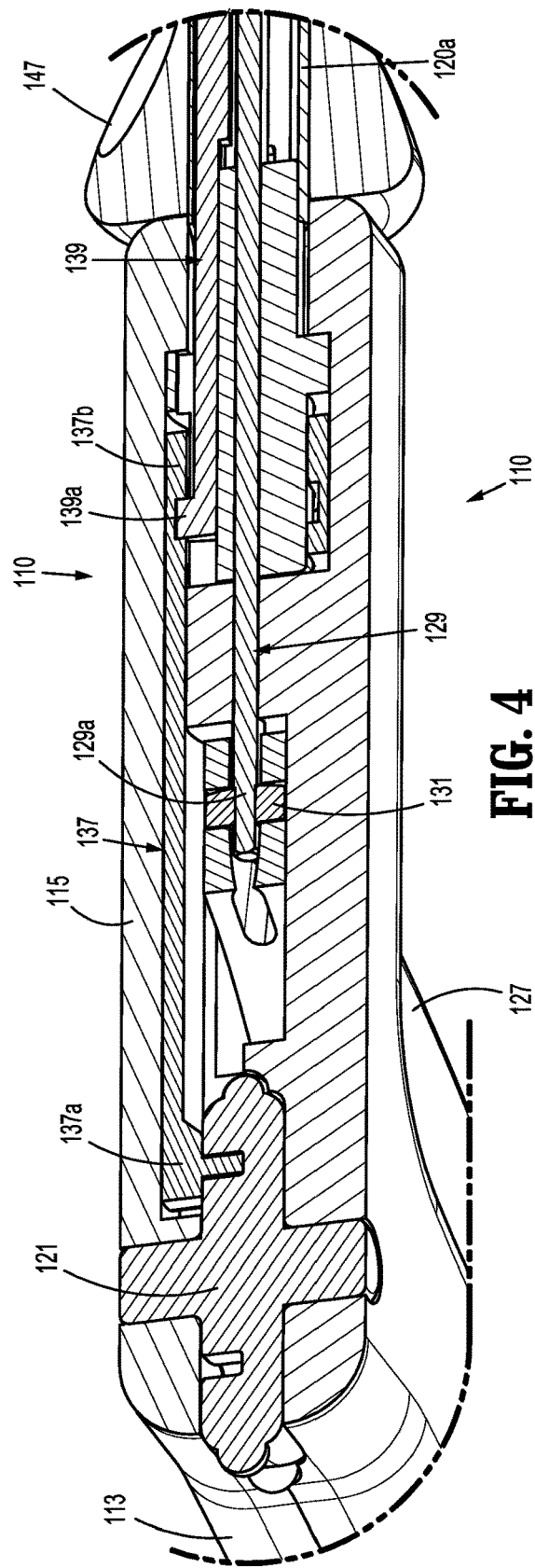

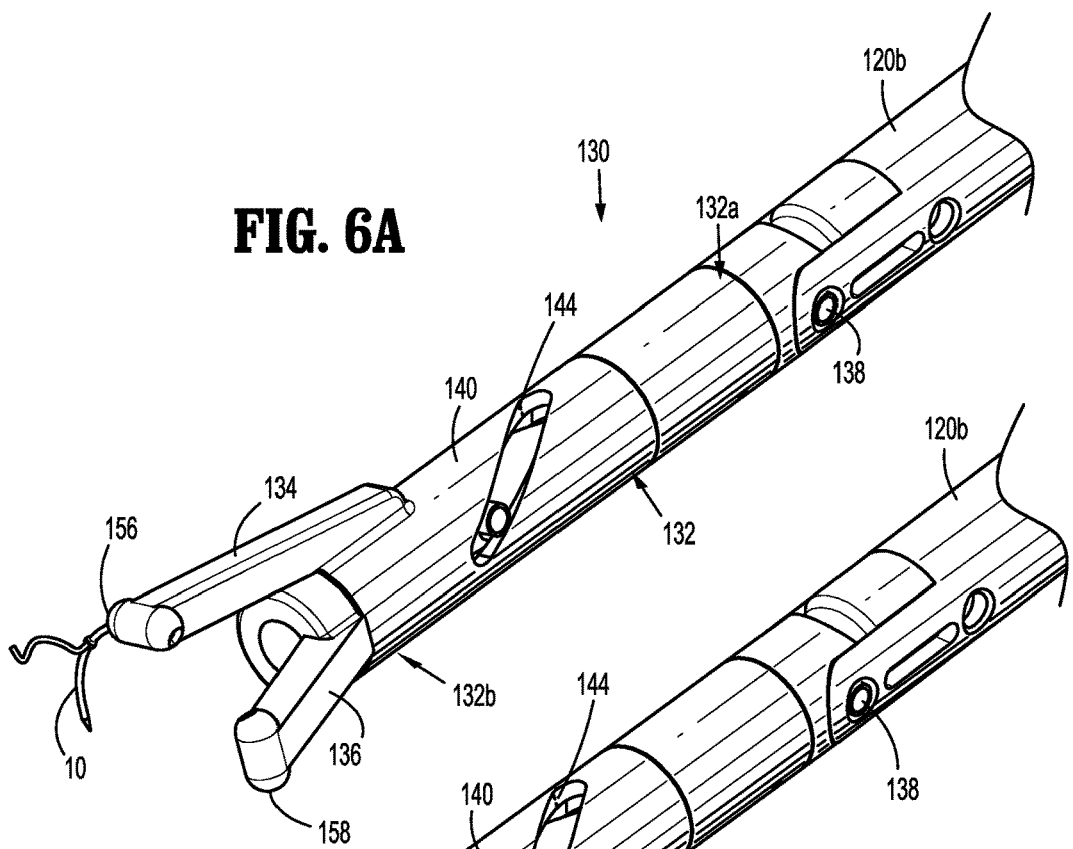
FIG. 6A
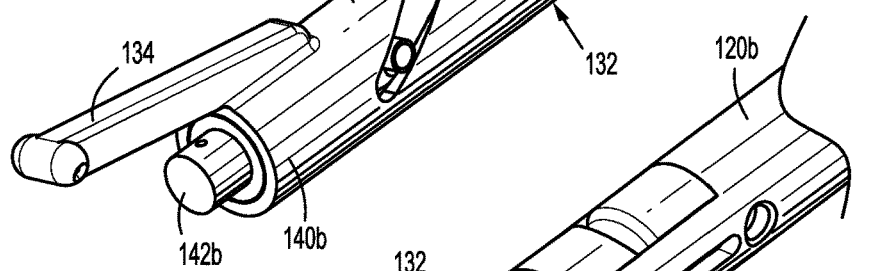
FIG. 6B
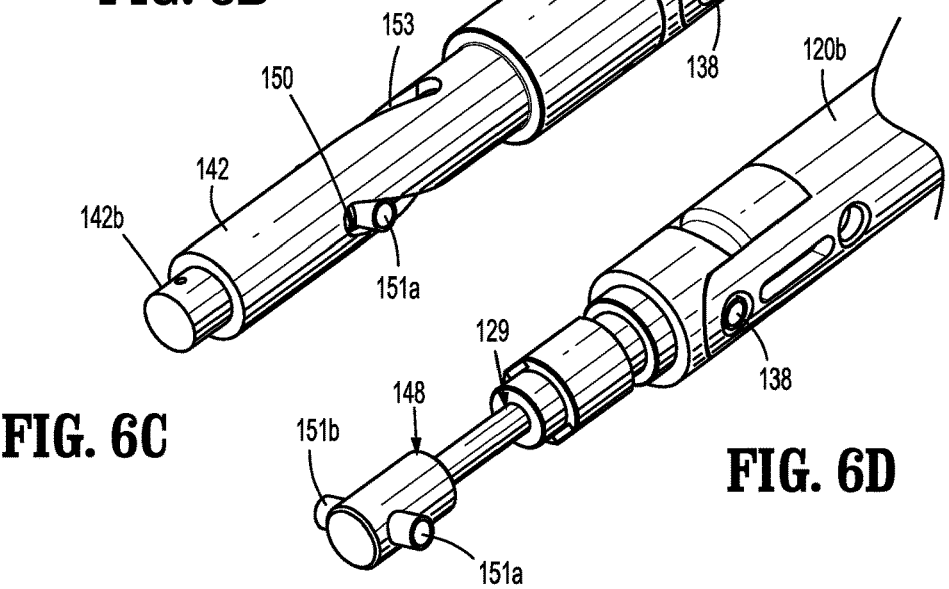
FIG. 6C
FIG. 6D

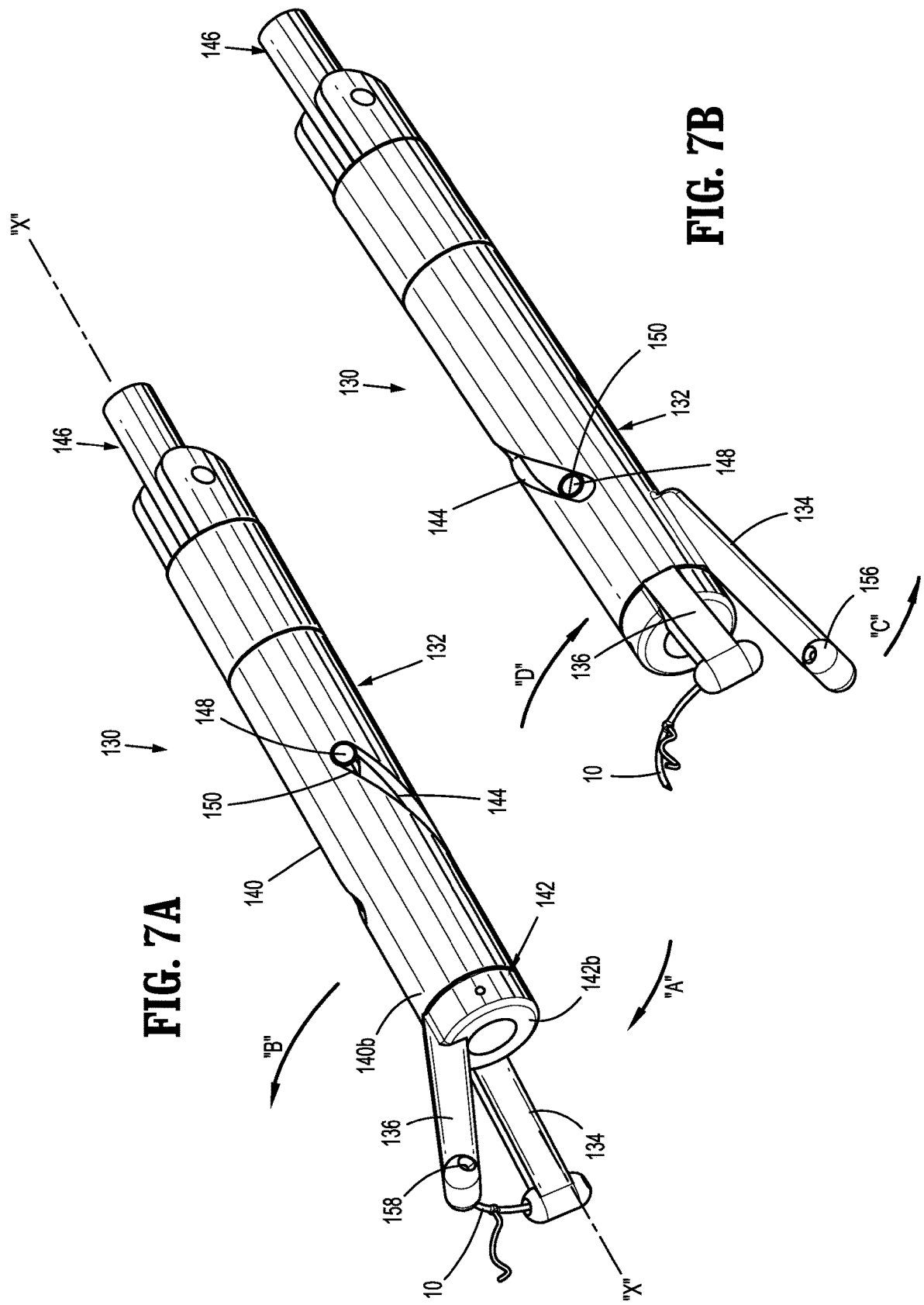

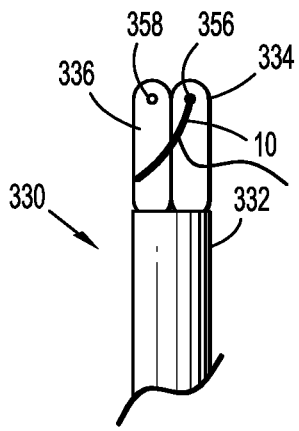 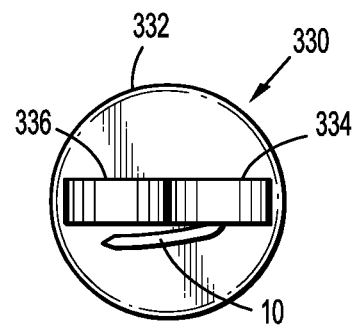
FIG. 10A     FIG. 10B
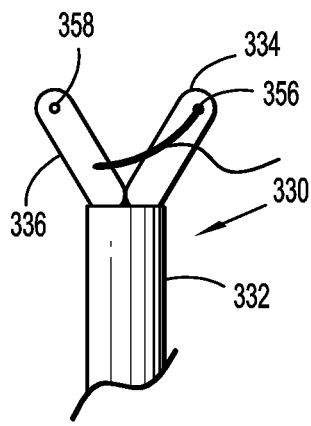 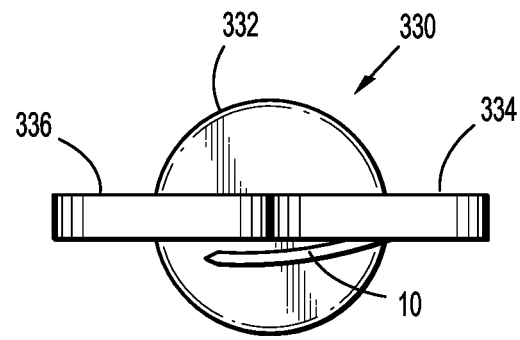
FIG. 11A     FIG. 11B
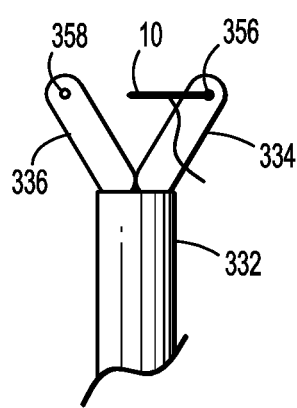 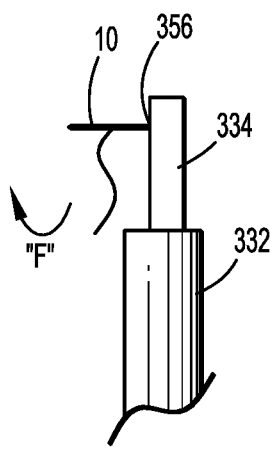 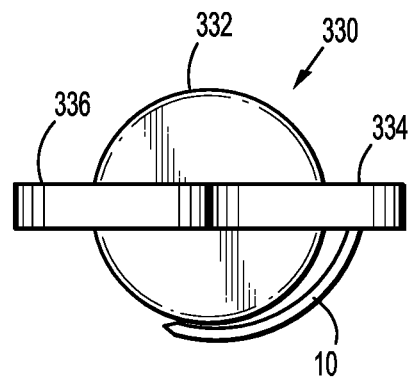
FIG. 12A     FIG. 12B     FIG. 12C

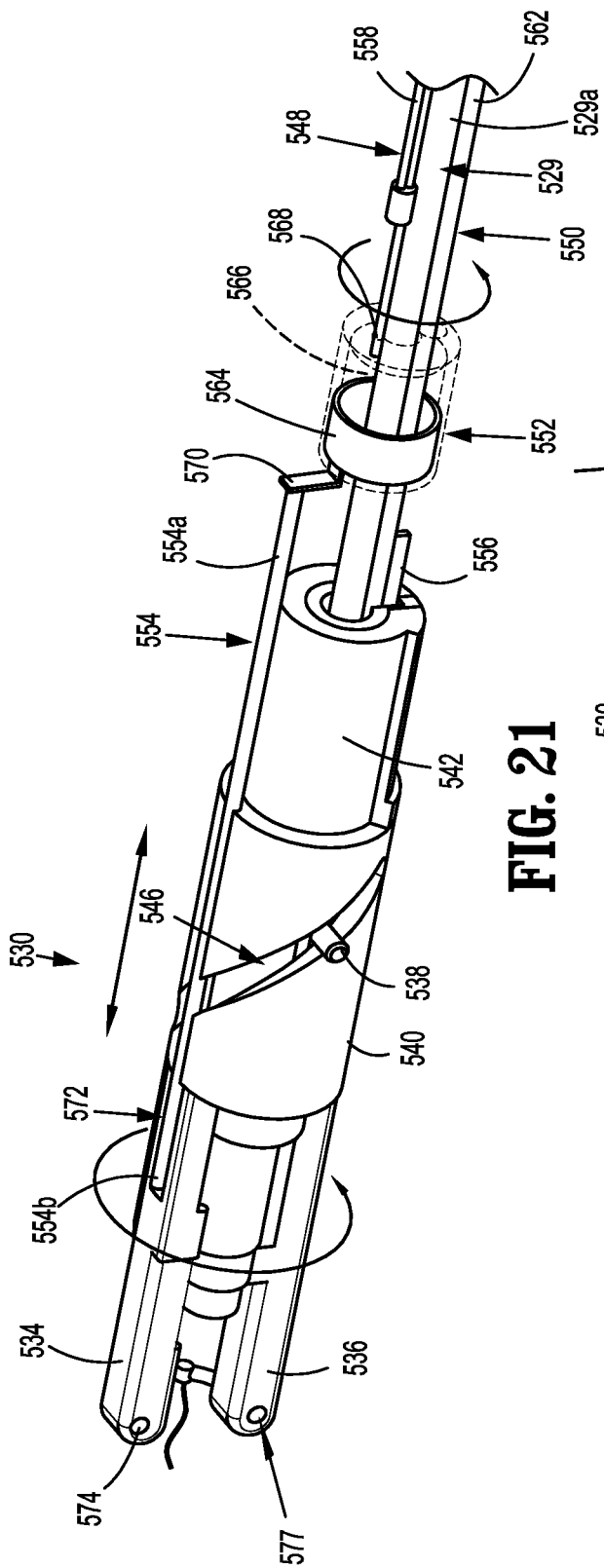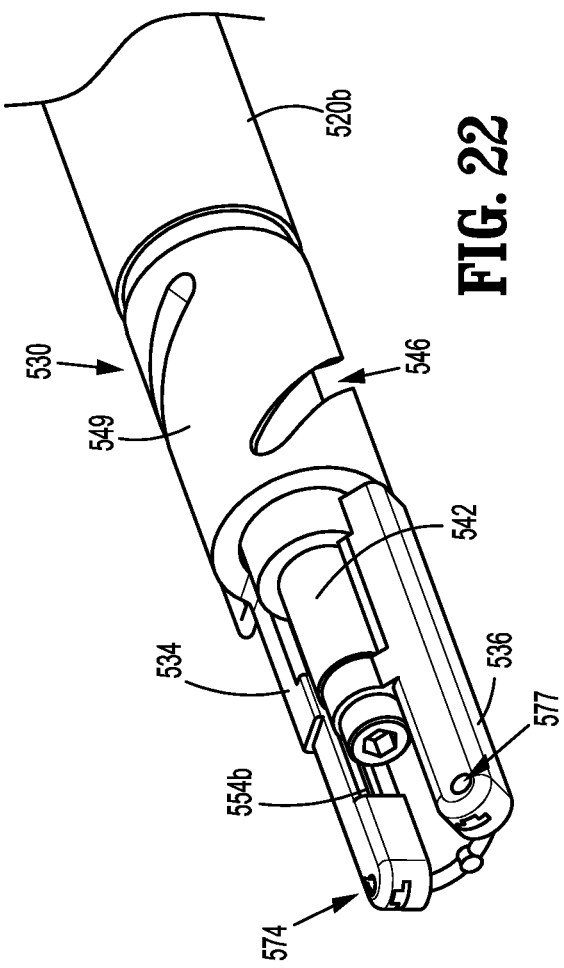

SURGICAL SUTURING INSTRUMENTS

CROSS-REFERENCE TO RELATED APPLICATIONS

This application is a Continuation-in-Part application of U.S. patent application Ser. No. 15/863,806, filed on Jan. 5, 2018, which claims the benefit of and priority to U.S. Provisional Application No. 62/462,512, filed on Feb. 23, 2017, the entire contents of each of which are incorporated by reference herein.

INTRODUCTION

Generally, endoscopic surgery involves incising through body walls for viewing and/or operating on a particular organ, such as, for example, the ovaries, uterus, gall bladder, bowels, kidneys, or appendix. Typically, trocars are utilized for creating an incision through which the endoscopic surgery is performed. Trocar tubes or cannula devices are extended into and left in place in the abdominal wall to provide access for endoscopic surgical tools. A camera or endoscope is inserted through a relatively large diameter trocar tube, which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, or the like, which are designed to fit through additional cannulas.

In many surgical procedures, including those involved in endoscopic surgery, it is often necessary to suture bodily organs or tissue. In the past, suturing of bodily organs or tissue through endoscopic surgery was achieved through the use of a sharp metal suture needle which had attached at one of its ends a length of suture material. The surgeon would cause the suture needle to penetrate and pass through bodily tissue, pulling the suture material through the bodily tissue. Once the suture material was pulled through the bodily tissue, the surgeon proceeded to tie a knot in the suture material. The knotting of the suture material allowed the surgeon to adjust the tension on the suture material to accommodate the particular tissue being sutured and control approximation, occlusion, attachment or other conditions of the tissue. The ability to control tension is extremely important to the surgeon regardless of the type of surgical procedure being performed.

SUMMARY

In accordance with one aspect of the disclosure, a surgical suturing instrument is provided and includes a handle assembly, a shaft extending distally from the handle assembly and defining a longitudinal axis, an end effector, and a first elongate locking element. The end effector includes a first jaw member and a second jaw member. The first jaw member is coupled to a distal end portion of the shaft and configured to rotate relative to and about the longitudinal axis of the shaft. The first jaw member defines a hole and a longitudinally-extending groove in communication with the hole. The hole is configured for detachable receipt of a curved needle. The second jaw member is coupled to a distal end portion of the shaft and defines a hole configured for detachable receipt of the curved needle. The first elongate locking element has a distal end portion slidably received in the groove. The first elongate locking element is configured to move between a proximal, non-locking position in which the distal end portion of the first elongate locking element is disposed proximally of the hole of the first jaw member, and a distal, locking position in which the distal end portion of the first elongate locking element is disposed within the hole of the first jaw member for locking the curved needle to the first jaw member.

In aspects, the second jaw member may define a longitudinally-extending groove in communication with the hole of the second jaw member.

In some aspects, the surgical suturing instrument may include a second elongate locking element having a distal end portion slidably received in the groove of the second jaw member. The second elongate locking element may be configured to move between a proximal, non-locking position in which the distal end portion of the second elongate locking element is disposed proximally of the hole of the second jaw member for releasing the curved needle, and a distal, locking position in which the distal end portion of the second elongate locking element is disposed within the hole of the second jaw member for locking the curved needle to the second jaw member.

In further aspects, the hole may define an axis that is perpendicular to an axis defined by the groove.

In other aspects, the surgical suturing instrument may include the curved needle. The curved needle may be configured for detachable receipt in the hole of each of the first and second jaw members.

In aspects, the curved needle may have a first end defining a first notch configured for receiving the distal end portion of the first elongate locking element when the first end is in the hole.

In some aspects, the curved needle may have a second end defining a second notch.

In further aspects, the surgical suturing instrument may further include a bearing assembly including an outer race and an inner race supported in the outer race. The first elongate locking element may have a proximal end portion coupled to the outer race or the inner race.

In other aspects, the surgical suturing instrument may include a push rod coupled to the other of the outer race or the inner race for moving the bearing assembly and the first elongate locking element between the proximal and distal positions.

In aspects, the end effector may include an outer body portion rotationally coupled to the distal end portion of the shaft. The first jaw member may be fixed to and extend from the outer body portion.

In some aspects, the end effector may include an inner body portion disposed within the outer body portion. The second jaw member may be coupled to a distal end portion of the inner body portion.

In further aspects, the surgical suturing instrument may include an actuation bar operably coupled to the handle assembly and configured to translate within the shaft in response to an actuation of the handle assembly. The outer body portion may define a cam slot having a portion of the actuation bar received therein such that translation of the actuation bar rotates the outer body portion and the first jaw member relative to the inner body portion and the second jaw member.

In accordance with another aspect of the disclosure, a surgical suturing instrument is provided and includes a handle assembly having a first trigger, a shaft extending distally from the handle assembly and defining a longitudinal axis, an end effector, and a first elongate locking element. The end effector includes a tubular outer body portion rotatably coupled to a distal end portion of the shaft, a first jaw member extending distally from the outer body portion, and a second jaw member. The first jaw member is configured to rotate with the outer body portion and relative to and about the longitudinal axis of the shaft. The first jaw member defines a hole configured for detachable receipt of a curved needle. The second jaw member is coupled to a distal end portion of the shaft and defines a hole configured for detachable receipt of the curved needle. The first elongate locking element has a proximal end portion coupled to the first trigger, and a distal end portion. The first elongate locking element is configured to move between a proximal, non-locking position in which the distal end portion of the first elongate locking element is disposed proximally of the hole of the first jaw member, and a distal, locking position in which the distal end portion of the first elongate locking element is disposed within the hole of the first jaw member for locking the curved needle to the first jaw member.

In aspects, the first jaw member may define a longitudinally-extending groove in communication with the hole of the first jaw member. The distal end portion of the first elongate locking element may be slidably disposed in the groove.

In some aspects, the surgical suturing instrument may include a second elongate locking element having a distal end portion slidably received in the second jaw member. The second elongate locking element may be configured to move between a proximal, non-locking position in which the distal end portion of the second elongate locking element is disposed proximally of the hole of the second jaw member for releasing the curved needle, and a distal, locking position in which the distal end portion of the second elongate locking element is disposed within the hole of the second jaw member for locking the curved needle to the second jaw member.

In further aspects, the surgical suturing instrument may include the curved needle. The curved needle may have a first end defining a first notch configured for receiving the distal end portion of the first elongate locking element when the first end is in the hole.

In other aspects, the curved needle may have a second end defining a second notch.

In aspects, the surgical suturing instrument may include a push rod and a bearing assembly. The push rod may have a proximal end portion coupled to the first trigger and may be configured to translate in response to an actuation of the first trigger. The bearing assembly may be disposed within the shaft and include an outer race and an inner race supported in the outer race. The proximal end portion of the first elongate locking element may be coupled to the outer race or the inner race and a distal end portion of the push rod may be coupled to the other of the outer race or the inner race for moving the bearing assembly and the first elongate locking element between the proximal and distal positions.

In some aspects, the end effector may include an inner body portion disposed within the outer body portion and rotationally fixed relative to the shaft. The second jaw member may be coupled to a distal end portion of the inner body portion.

In further aspects, the surgical suturing instrument may include an actuation bar operably coupled to a second trigger of the handle assembly and configured to translate within the shaft in response to an actuation of the second trigger. The outer body portion may define a cam slot having a portion of the actuation bar received therein such that translation of the actuation bar rotates the outer body portion and the first jaw member relative to the inner body portion and the second jaw member.

Further details and aspects of exemplary embodiments of the disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

The above and other objects and features of the disclosure will become apparent from the following description of embodiments given in conjunction with the accompanying drawings, in which:

FIG. 1 is a perspective view of a surgical suturing instrument in accordance with the principles of the disclosure;

FIG. 2 is a perspective view of a handle assembly of the surgical suturing instrument of FIG. 1;

FIG. 3 is a cross-sectional view, taken along line 3-3 of FIG. 1, of the surgical suturing instrument;

FIG. 4 is an enlarged view of detail 4 of FIG. 3 illustrating internal components of the handle assembly;

FIG. 6A is a perspective view of an end effector of the surgical suturing instrument of FIG. 1;

FIG. 6B is a perspective view, with parts removed, of the end effector of FIG. 6A;

FIG. 6C is a perspective view, with additional parts removed, of the end effector of FIG. 6B;

FIG. 6D is a perspective view, with additional parts removed, of the end effector of FIG. 6C;

FIG. 7A is a perspective view of the end effector of FIG. 6A illustrating jaw members thereof in a first position;

FIG. 7B is a perspective view of the end effector of FIG. 6A illustrating the jaw members in a second position;

FIG. 10A is a side view of an end effector of a surgical suturing instrument and a curved needle attached thereto illustrating jaw members of the end effector in a closed configuration with the curved needle in a stowed position;

FIG. 10B is a top view of the end effector of FIG. 10A;

FIG. 11A is a side view of the end effector of FIG. 10A illustrating the jaw members of the end effector in an open configuration;

FIG. 11B is a top view of the end effector of FIG. 11A;

FIGS. 12A and 12B are alternate side views of the end effector of FIG. 10A illustrating the jaw members in an open configuration with the curved needle splayed outwardly;

FIG. 12C is a top view of the end effector of FIGS. 12A and 12B;

FIG. 21 is a side perspective view illustrating an end effector and a bearing assembly of the surgical suturing instrument shown in FIG. 20;

FIG. 22 is a side perspective view illustrating jaw members of the end effector of FIG. 21 in an approximated state for transferring a curved needle;

DETAILED DESCRIPTION

Figure 5:
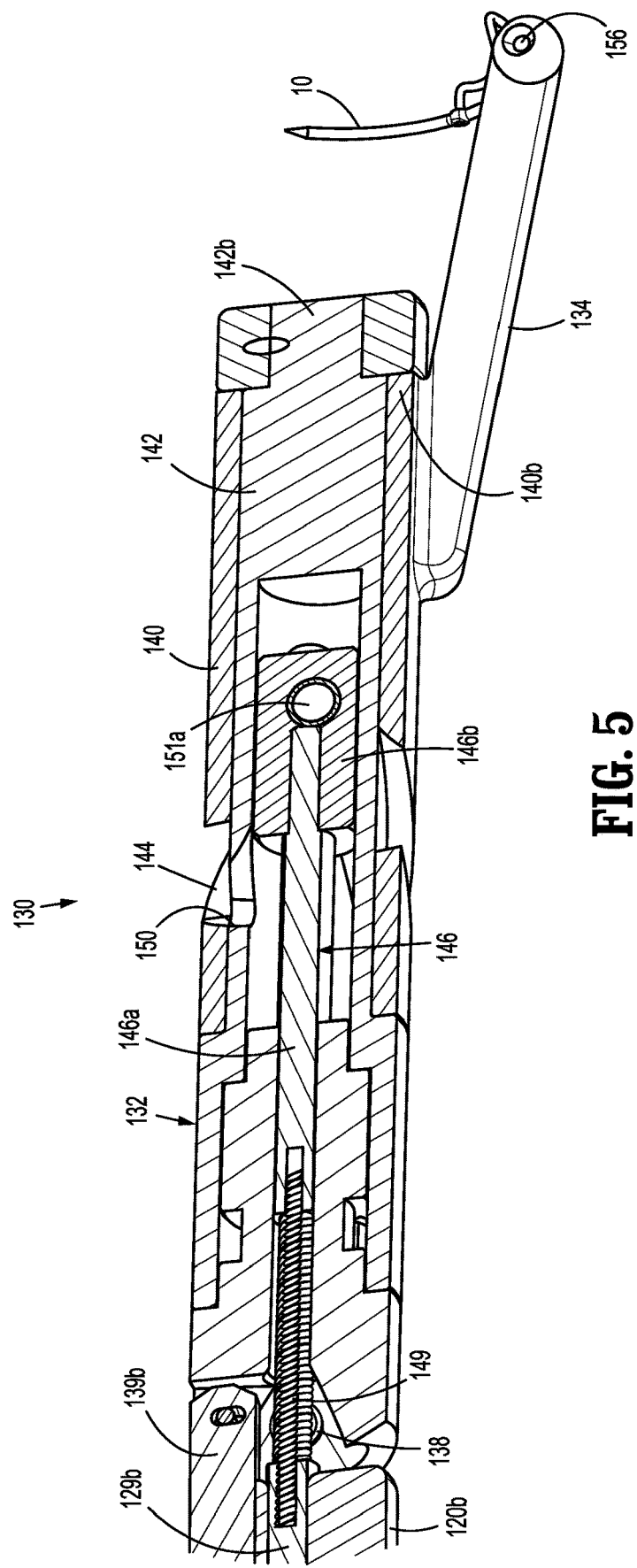
FIG. 5 is an enlarged view of detail 5 of FIG. 3 illustrating internal components of an end effector of the surgical suturing instrument.
Figure 8A:
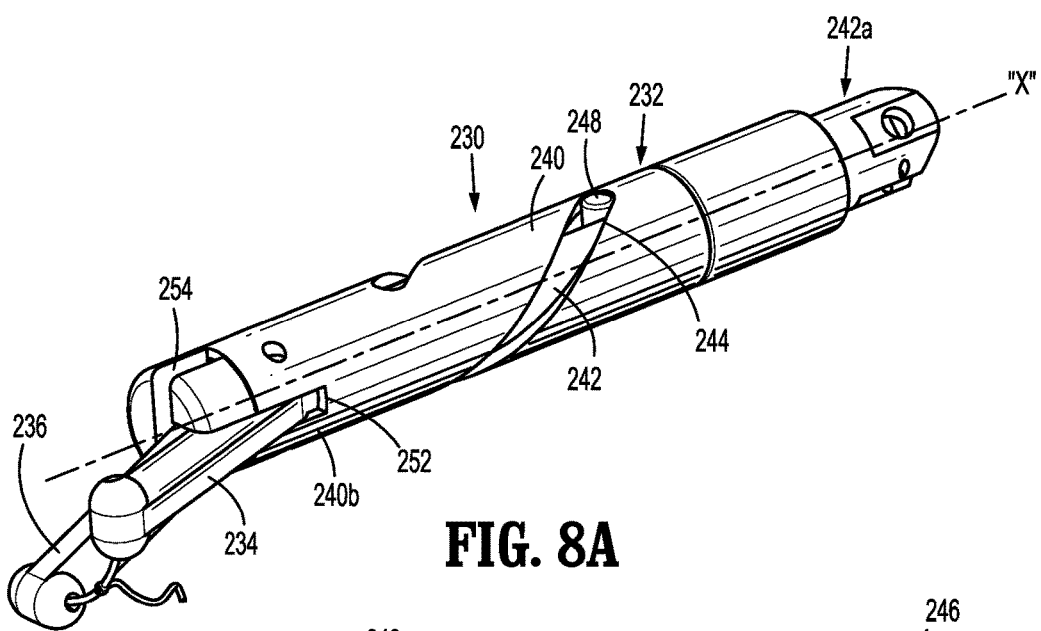
FIG. 8A is a perspective view of another embodiment of an end effector of a surgical suturing instrument.
Figure 8B:
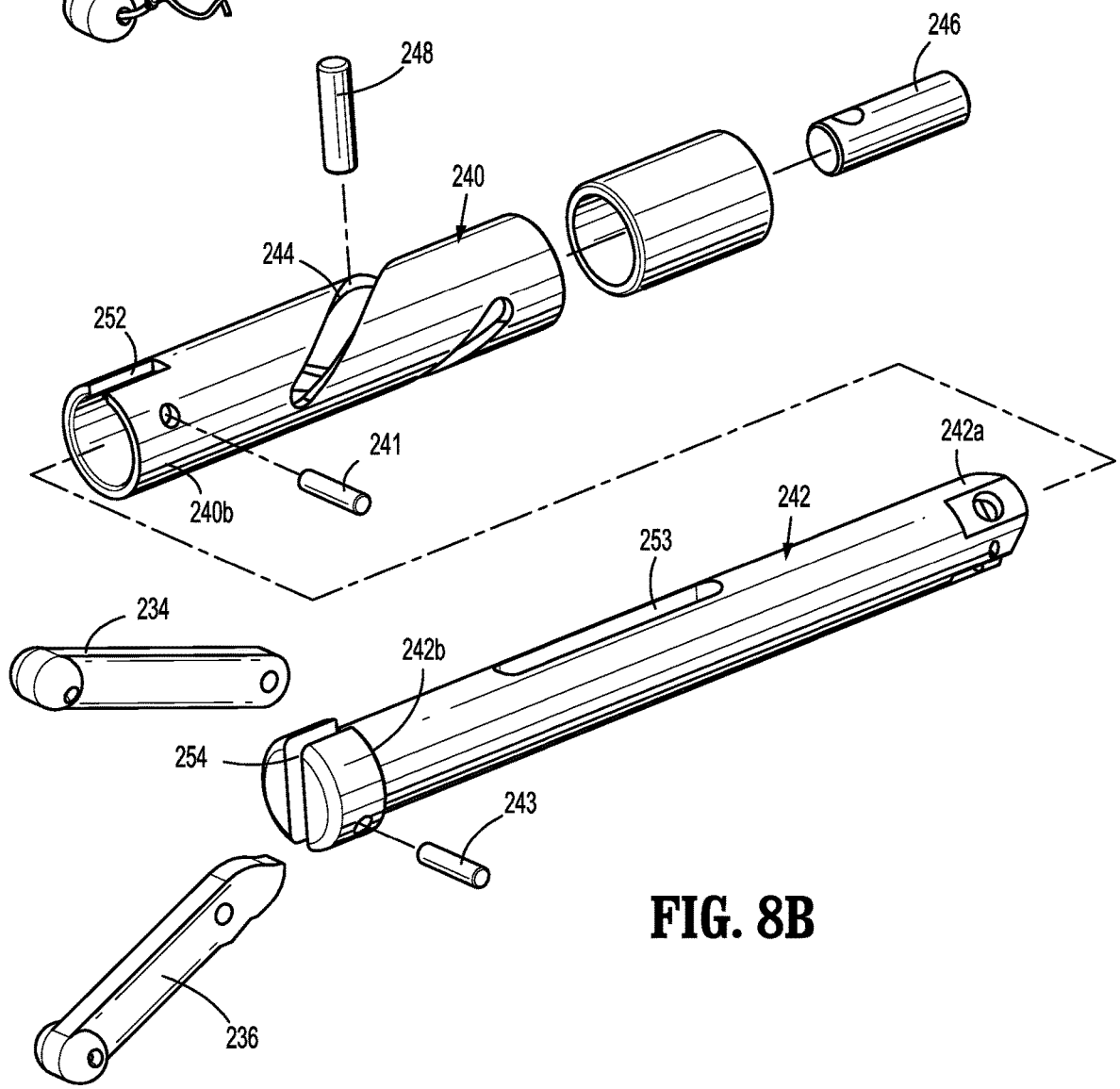
FIG. 8B is a perspective view, with parts separated, of the end effector of FIG. 8A.

Various embodiments of the presently disclosed surgical suturing instruments for endoscopic, laparoscopic, endoluminal, and/or transluminal suturing will now be described in detail with reference to the drawings, wherein like reference numerals identify similar or identical elements. In the drawings and in the description that follows, the term "proximal" will refer to the portion of the surgical suturing instrument, or component thereof, that is closer to the user, while the term "distal" will refer to the portion of the surgical suturing instrument, or component thereof, that is farther from the user.

The minimally invasive surgical suturing instruments of the disclosure generally include a handle assembly or other suitable actuating mechanism, an elongate tubular body or shaft, and an end effector. The handle assembly is connected to a proximal portion of the elongate tubular body, and the end effector is operatively supported at a distal portion of the elongate tubular body, which allows the end effector to articulate in response to actuation of articulation cables, tethers, wires, rods, or the like. The end effector includes a curved suture needle and a pair of jaw members. In operation, the suture needle is passed back and forth through tissue from one jaw to another jaw by rotating one or both of the jaw members about a longitudinal axis defined by the elongate tubular body. The surgical suturing instruments described herein are configured for use with a curved needle having a suture attached thereto. The needle may include a groove formed near each end thereof. A suture may be secured to the surgical needle at a location between the grooves. The suture of needle may include a one-way or barbed suture, wherein the suture includes an elongated body having a plurality of barbs extending therefrom. The barbs are oriented in such a way that the barbs cause the suture to resist movement in an opposite direction relative to the direction in which the barb faces.

With reference to FIG. 1, a surgical suturing instrument in accordance with an embodiment of the disclosure is identified generally as 100. Surgical suturing instrument 100 is adapted to be particularly useful in endoscopic or laparoscopic procedures, wherein an end effector 130 of the surgical suturing instrument 100 is insertable into a surgical site, via a cannula assembly or the like. Surgical suturing instrument 100 includes a handle assembly 110, a shaft 120 extending distally from handle assembly 110, and an end effector 130 that extends from a distal portion 120b of shaft 120.

With reference to FIGS. 1-4, handle assembly 110 of surgical suturing instrument 100 includes a handle housing 111 that supports both an actuation assembly 117 and an articulation assembly 119. Handle housing 111 has a fixed handle 113 and a barrel portion 115 extending substantially perpendicularly from handle 113. Handle 113 has an articulation wheel 121 of articulation assembly 119 rotatably supported therein or thereon. Barrel portion 115 of handle housing 111 has a cavity 125 for slidable receipt of actuation assembly 117.

Actuation assembly 117 of handle assembly 110 includes a trigger 127, an actuation shaft 129, and a pin 131 attached to a proximal portion 129a of actuation shaft 129. Pin 131 is fixed to trigger 127 and proximal portion 129a of actuation shaft 129 is fixed to pin 131 such that movement of trigger 127 relative to handle housing 111 moves pin 131 and, in turn, actuation shaft 129, through barrel portion 115. Actuation shaft 129 of actuation assembly 117 extends perpendicularly from pin 131, through cavity 125 of barrel portion 115, and terminates in a distal portion 129b that is operably coupled to end effector 130 in a manner to rotate jaw members 134, 136 of the end effector 130 upon actuation of trigger 127, as will be described in detail below.

Articulation assembly 119 of handle assembly 110 includes a rotation wheel 121 and a first rod or shaft 137 operably coupled to rotation wheel 121 at a proximal portion 137a of first rod 137. First rod 137 has a distal portion 137b attached to a proximal portion 139a of a second rod 139 that extends through shaft 120. Second rod 139 of articulation assembly 119 has a distal portion 139b (FIG. 5) pinned to end effector 130 at a location adjacent an articulation joint, for example, an articulation pin 138. In particular, second rod 139 of articulation assembly 119 is spaced radially outward of articulation pin 138 (i.e., offset from a central longitudinal axis of shaft 120) such that longitudinal movement of first and second rods 137, 139, via rotation of rotation wheel 121, effects an articulation of end effector 130 relative to shaft 120 about articulation pin 138 in one of two opposing directions.

Surgical suturing instrument 100 further includes a rotation knob or rotation housing 147. Rotation knob 147 is rotationally fixedly disposed about a proximal portion 120a of shaft 120 such that a rotation of rotation knob 147 effects a rotation of shaft 120 about longitudinal axis "X" of shaft 120.

With reference to FIGS. 1 and 4-7B, shaft 120 of surgical suturing instrument 100 has a proximal portion 120a disposed within cavity 125 of handle housing 111 and a distal portion 120b. End effector 100 of surgical suturing instrument 100 is pivotably coupled to distal portion 120b of shaft 120. End effector 130 generally includes an elongated body portion 132 and first and second jaw members 134, 136 each non-pivotably coupled to a distal portion of body portion 132. In some embodiments, jaw members 134, 136 may be pivotably coupled to the distal portion of body portion 132. Body portion 132 has a proximal portion pivotably coupled to distal portion 120b of shaft 120 of surgical suturing instrument 100 via the articulation pin 138 mentioned above. As such, end effector 130 is articulatable relative to shaft 120 about the articulation pin 138 via the articulation assembly 119 (FIG. 1) described above.

In some embodiments, instead of articulation assembly 119 being responsible for articulating end effector 130, body portion 132 may be pivoted or articulated relative to shaft 120 using a pair of cables (not shown) that extend from handle assembly 110 and connect to opposite sides of body portion 132 of end effector 130. In operation, as one cable is pulled proximally, the other cable is pushed distally (or let out) to articulate end effector 130 relative to shaft 120.

With continued reference to FIGS. 1 and 4-7B, body portion 132 of end effector 130 includes a rotatable outer shaft 140 and a rotatable inner shaft 142 disposed within outer shaft 140. Outer shaft 140 has first jaw member 134 coupled to a distal portion thereof, and inner shaft 142 has second jaw member 136 coupled to a distal portion thereof such that first and second jaw members 134, 136 rotate with a rotation of inner and outer shafts 140, 142 about a longitudinal axis defined by body portion 132, as will be described below. A distal portion 142b of inner shaft 142 extends distally beyond a distal portion 140b of outer shaft 140. First jaw member 134 is longer than second jaw member 136 by a length substantially equal to a length that distal portion 142b of inner shaft 142 extends distally beyond distal portion 140b of outer shaft 140. As such, the distal ends of first and second jaw members 134, 136 are aligned with one another to facilitate an exchange of a suture needle 10 therebetween.

Outer shaft 140 of body portion 132 defines a helical cam slot 144 formed therein. In some embodiments, cam slot 144 may assume a variety of patterns, for example, zig-zag, undulating, or the like. End effector 130 includes an actuation bar 146 that is configured to translate along the longitudinal axis of body portion 132 in response to an actuation of trigger 127 of handle assembly 110. In particular, actuation bar 146 has a proximal portion 146a operably coupled to distal portion 129b (FIG. 5) of actuation shaft 129 of handle assembly 110. In some embodiments, actuation shaft 129 of handle assembly 110 and actuation bar 146 of end effector 130 are integrally formed with one another. Actuation shaft 129 of handle assembly 110 is coupled to actuation bar 146 via a flexible elongate member 149 disposed at a location adjacent articulation pin 138 of shaft 120 so that as end effector 130 articulates relative to shaft 120, actuation bar 146 bends relative to actuation shaft 129 about flexible elongate member 149. In some embodiments, actuation shaft 129 and actuation bar 146 are each formed from a flexible material permitting actuation bar 146 to flex relative to actuation shaft 129 during articulation of end effector 130

Actuation bar 146 of end effector 130 has a distal portion in the form of a T-shaped cam 146b having a first projection 151a that is slidably received within cam slot 144 of outer shaft 140. Upon the axial translation of actuation bar 146 relative to body portion 132 of end effector 130, first projection 151a of cam 146b of actuation bar 146 moves through cam slot 144 of outer shaft 140 to rotate outer shaft 140 about the longitudinal axis of body portion 132 and, in turn, rotate first jaw member 134.

Inner shaft 142 of body portion 132 also defines a helical cam slot 150 formed therein. Cam slot 150 of inner shaft 142 is angled relative to cam slot 144 of outer shaft 140 (e.g., cam slots 144, 150 run in opposing helical directions relative to one another). Projection 151a of cam 146b of actuation bar 146 also extends through cam slot 150 of inner shaft 142. Since cam slots 144, 150 of outer and inner shafts 140, 142 run in opposing directions, as actuation bar 146 is translated within body portion 132 of end effector 130, outer and inner shafts 140, 142 are rotated in opposite directions and, in turn, first and second jaw members 134, 136 are rotated in opposite directions.

Inner shaft 142 may define another cam slot 153 disposed on an opposite side of inner shaft 142 from cam slot 150. A second projection 151b of cam 148 may extend through second cam slot 153 of inner shaft 142 to facilitate rotation of inner shaft 142 and resist rotation of actuation bar 146.

In some embodiments, surgical suturing instrument 100 may include a second actuation bar (not shown) that is operably coupled to another trigger (not shown) of handle assembly 110. Instead of cam 146b of actuation bar 146 extending through cam slot 150 of inner shaft 142, the second actuation bar may have a projection or cam at its distal end that extends through cam slot 150 of inner shaft 142. As such, inner and outer shafts 140, 142 may be independently rotated relative to one another using their respective actuation bars.

With reference to FIGS. 7A and 7B, first and second jaw members 134, 136 each have a proximal portion and a distal portion. The proximal portion of each of the first and second jaw members 134, 136 is coupled to outer shaft 140 and inner shaft 142, respectively. In some embodiments, first and second jaw members 134, 136 may be pivotably connected to body portion 132 via a joint, for example, a hinge or a knuckle/clevis. The distal portion of each of the first and second jaw members 134, 136 defines a hole or aperture 156, 158 therein sized and dimensioned for detachable and/or selective receipt of an end of a curved suture needle 10. Holes 156, 158 extend entirely through a thickness of first and second jaw members 134, 136, respectively. In some embodiments, holes 156, 158 may only extend partially through a thickness of first and second jaw members 134, 136.

Holes 156, 158 are configured to selectively retain an end of curved needle 10 therein such that needle 10 may be passed to and from first and second jaw members 134, 136 during a surgical procedure. In particular, each of the holes 156, 158 may have disposed therein a touch latch or push latch (not explicitly shown) having pivotable engagement portions or hooks for selectively engaging and releasing opposing ends of curved needle 10. In addition, each opposing end of the curved needle 10 may have a hole or recess defined therein configured to selectively engage the push latch disposed in each of the holes 156, 158 of jaw members 134, 136.

For example, with jaw members 134, 136 in a starting position, a first end of curved needle 10 is engaged to the push latch of first jaw member 134 such that the first end of curved needle 10 is temporarily fixed to first jaw member 134, while second jaw member 136 is spaced from first jaw member 134 and disengaged from a second end of curved needle 10. Upon approximation of jaw members 134, 136, the second end of curved needle 10 engages an interior wall that defines hole 158 of second jaw member 136 to apply pressure on the push latches of both the first and second jaw members 134, 136. This pressure applied on the push latches by opposing first and second ends of the curved needle 10 actuates the push latches to simultaneously cause the push latch of first jaw member 134 to disengage the first end of the curved needle 10 and the push latch of the second jaw member 136 to engage the second end of the curved needle 10. Upon spacing or separating the first and second jaw members 134, 136, the curved needle 10 stays attached to the second jaw member 136 and is released from the first jaw member 134.

In some embodiments, rather than holes 156, 158 having push latches for selectively attaching and detaching curved needle 10 to jaw members 134, 136, holes 156, 158 may have a magnetic semiconductor (not shown) disposed therein. The semiconductors are of the type that can have their magnetism selectively turned on and off by selectively applying a voltage thereto using the phenomenon known as electrically induced ferromagnetism. In particular, surgical suturing instrument 100 may include two wires (not shown) extending from a generator (not shown) disposed in handle assembly 110 (or coupled to handle assembly 110) and terminating at a respective semiconductor in jaw members 134, 136. The generator of handle assembly 110 may apply a voltage to the semiconductor of first jaw member 134 via the wire to turn on the magnetism of the semiconductor of first jaw member 134 when it is desired to have curved needle 10 retained in first jaw member 134. To pass curved needle 10 from first jaw member 134 to second jaw member 136, the magnetism of the semiconductor of first jaw member 134 is turned off to release a metallic first end of curved needle 10 from first jaw member 134. Concurrently with turning the magnetism of the semiconductor of first jaw member 134 off, the magnetism of the semiconductor of second jaw member 136 is turned on to retain a metallic second end of curved needle 10 in hole 158 of second jaw member 136.

In some embodiments, instead of using magnetic semiconductors to selectively retain curved needle 10 in jaw members 134, 136, surgical suturing instrument 100 may include wires or thin cables (not shown) that extend through channels defined through first and second jaw members 134, 136. The wires are fabricated from an elastic, malleable material, for example, an elastomer, a shape memory alloy or a shape memory plastic. The wires are configured to move in opposite longitudinal directions through the channels defined through jaw members 134, 136 to selectively pass in and out of holes 156, 158 of first and second jaw members 134, 136. Distal ends of the wires are configured to interlock with an aperture or indentation (not shown) defined in opposite ends of curved needle 10 to prevent curved needle 10 from detaching from the selected jaw member 134 or 136. In particular, as one wire moves into a hole 156 or 158 of its respective jaw member 134 or 136, the other wire moves out of the hole 156 or 158 of its respective jaw member 134 or 136. In this way, curved needle 10 may be detachably retained within either of the first and second jaw members 134, 136 due to the engagement of a distal end of one of the wires with an end of the curved needle 10.

In operation, to perform a minimally invasive procedure involving a suturing of tissue, for example, a hernia repair, an access tube or cannula is positioned through surface tissue of a patient to gain access to the surgical site within a body of the patient. Surgical suturing instrument 100 is passed through the cannula to position jaw members 134, 136, with curved needle 10, adjacent the subject tissue. To pass curved needle 10 (having a suture attached thereto) through the tissue to suture the tissue, jaw members 134, 136 are rotated from a spaced-apart position to an approximated position.

To rotate jaw members 134, 136 about the longitudinal axis of body portion 132 of end effector 130, trigger 127 of handle assembly 110 is actuated to move actuation shaft 129 of handle assembly 110 in a proximal direction. Due to actuation bar 146 of end effector 130 being coupled to actuation shaft 129 of handle assembly 110, proximal movement of actuation shaft effects proximal movement of actuation bar 146 through body portion 132. Cam 146b of actuation bar 146 moves through cam slots 144, 150 of outer and inner shafts 140, 142, respectively, to drive a rotation of outer and inner shafts 140, 142 in opposing directions, indicated by arrows "A" and "B" of FIG. 7A. Since jaw members 134, 136 are coupled to outer and inner shafts 140, 142, respectively, jaw members 134, 136 are rotated with outer and inner shafts 140, 142 toward one another to drive needle 10 along a circular pathway around longitudinal axis "X" of body portion 132 through the tissue.

Rotation of jaw members 134, 136 is continued until hole 158 of second jaw member 136 receives an end of curved needle 10. Curved needle 10 is transferred from first jaw member 134 to second jaw member 136 using the touch latches described above, or any other suitable mechanism. With curved needle 10 connected to second jaw member 136, trigger 127 is released, allowing a spring (not shown) to move trigger 127 to the unactuated position, thereby moving actuation shaft 129 of handle assembly in a distal direction back to the starting position. Distal movement of the actuation shaft 129 pushes or drives actuation bar 146 of end effector 130 in the distal direction through body portion 132 of end effector 130. Movement of actuation bar 146 in the distal direction moves cam 146b of actuation bar 146 through cam slots 144, 150 of outer and inner shafts 140, 142 to drive a rotation of outer and inner shafts 140, 142, and in turn, first and second jaw members 134, 136, away from one another, in the direction indicated by arrows "C" and "D" in FIG. 7B. This process may be continued until the subject tissue is sutured.

With reference to FIGS. 8A-9E, another embodiment of an end effector 230 of a surgical suturing instrument is provided. End effector 230 is similar to end effector 130 described above with reference to FIGS. 1-7B with a difference being that end effector 230 is configured to rotate only one of its jaw members about a longitudinal axis defined by end effector 230. Thus, end effector 230 will only be described in the detail necessary to elucidate particular differences between the embodiments.

End effector 230 may be remotely operable by a handle assembly, for example, the handle assembly 110 of FIG. 1, or any other suitable actuating mechanism. End effector 230 generally includes an elongated body portion 232 and first and second jaw members 234, 236 each pivotably coupled to a distal portion of body portion 232. Unlike end effector 130 described above, end effector 230 is configured to rotate only first jaw member 234 about a longitudinal axis "X" defined by body portion 232 rather than both first and second jaw members 234, 236.

Body portion 232 of end effector 230 has a proximal portion configured to be pivotably coupled to a distal portion of a shaft, for example, shaft 120 of FIG. 1. As such, end effector 230 is articulatable relative to shaft 120. Body portion 232 of end effector 230 includes a rotatable outer shaft 240 and an inner shaft 242 disposed within outer shaft 240. Outer shaft 240 has first jaw member 234 pivotably coupled to a distal portion 240b thereof via a pivot pin 241, and inner shaft 242 has second jaw member 236 pivotably coupled to a distal portion 242b thereof via a pivot pin 243. Distal portion 242b of inner shaft 242 extends distally beyond distal portion 240b of outer shaft 240 to allow for second jaw member 236 to pivot outwardly from body portion 232 without interference from distal portion 240b of outer shaft 240.

Outer shaft 240 defines a helical cam slot 244 formed therein. In some embodiments, cam slot 244 may assume a variety of patterns, for example, zig-zag, undulating, or the like. End effector 230 includes an actuation bar 246 that is configured to translate along longitudinal axis "X" of body portion 232 in response to an actuation of trigger 127 of handle assembly 110 (FIG. 1). The actuation bar 246 extends through a pin or cam 248 that is slidably received within cam slot 244 of outer shaft 240. Upon the axial translation of the actuation bar 246 relative to body portion 232 of end effector 230, cam 248 is moved through cam slot 244 of outer shaft 240 to cause outer shaft 240 to rotate about longitudinal axis "X" of body portion 232 and, in turn, rotate first jaw member 234 to or away from second jaw member 236.

Figure 9A:
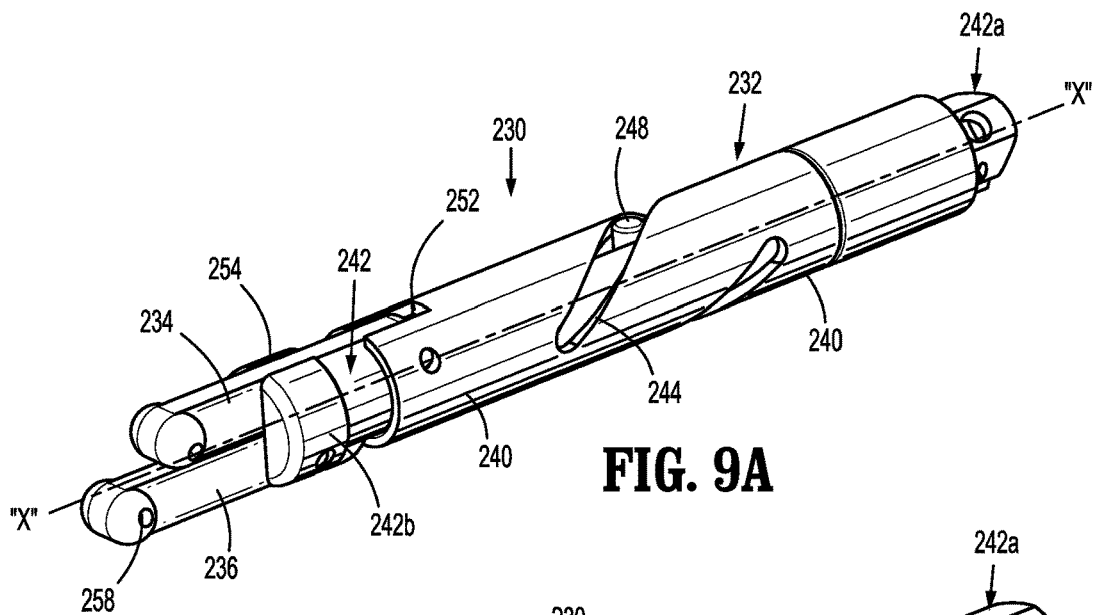
FIG. 9A is a perspective view of the end effector of FIG. 8A illustrating jaw members of the end effector in a closed configuration.

Distal portion 240b of outer shaft 240 defines a longitudinally-extending slot 252. When first jaw member 234 is in the closed configuration, as shown in FIG. 9A, first jaw member 234 extends through slot 252 of outer shaft 240. Inner shaft 242 defines a longitudinally extending slot 253 in an intermediate portion thereof. Cam 248 extends through slot 253 of inner shaft 242 and is guided along the longitudinal axis "X" by slot 253 during actuation of cam 248 by the actuation bar 246. Inner shaft 242 also defines a transversely-extending slot 254 located at distal portion 242b of inner shaft 242. When outer and inner shafts 240, 242 are in a first position, as shown in FIG. 9A, slot 254 of inner shaft 242 is aligned with slot 252 of outer shaft 240 to form one continuous elongated slot for receipt of first jaw member 234. In some embodiments, distal portion 240b of outer shaft 240 and/or distal portion 242b of inner shaft 242 may have additional slots formed therein.

Figure 9B:
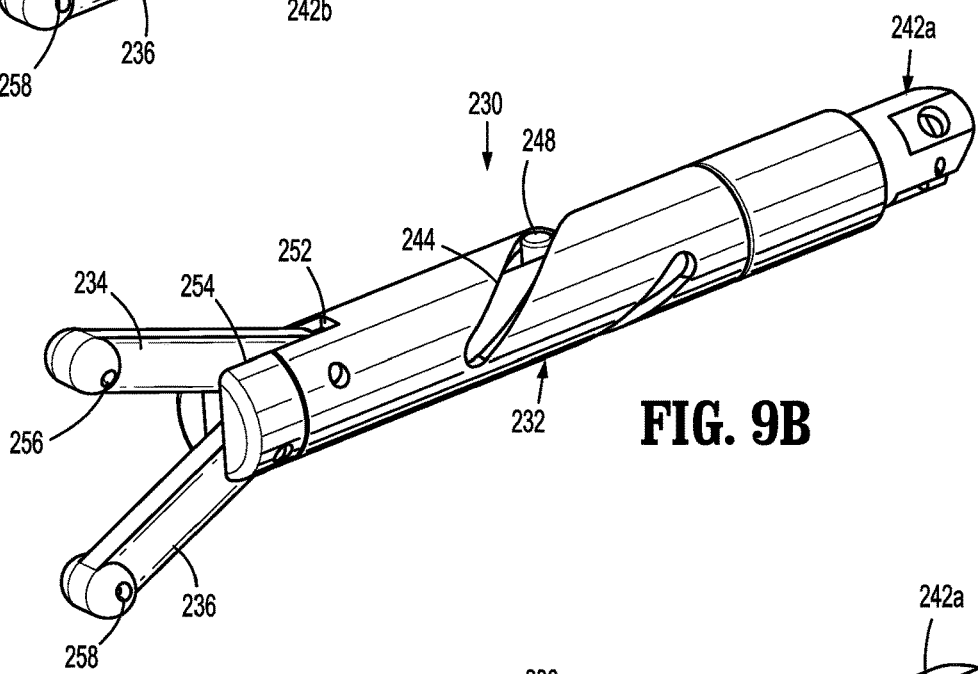
FIG. 9B is a perspective view of the end effector of FIG. 9A illustrating the jaw members in an open configuration.
Figure 9C:
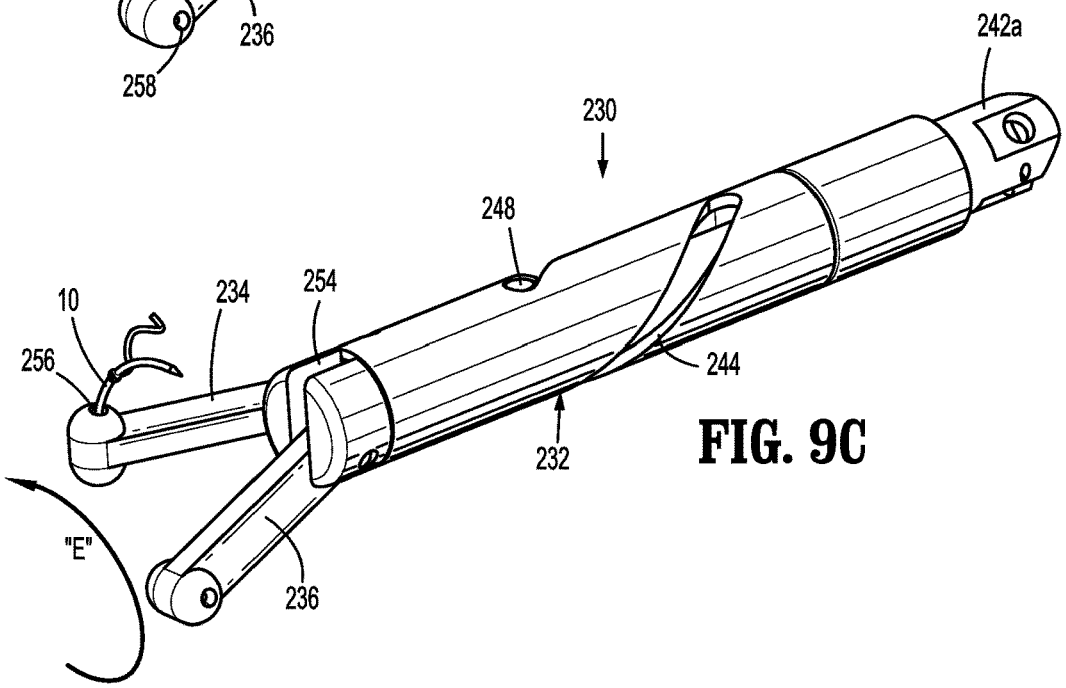
FIG. 9C is a perspective view of the end effector of FIG. 9A illustrating the jaw members after a first jaw member of the jaw members has been rotated in a first direction.
Figure 9D:
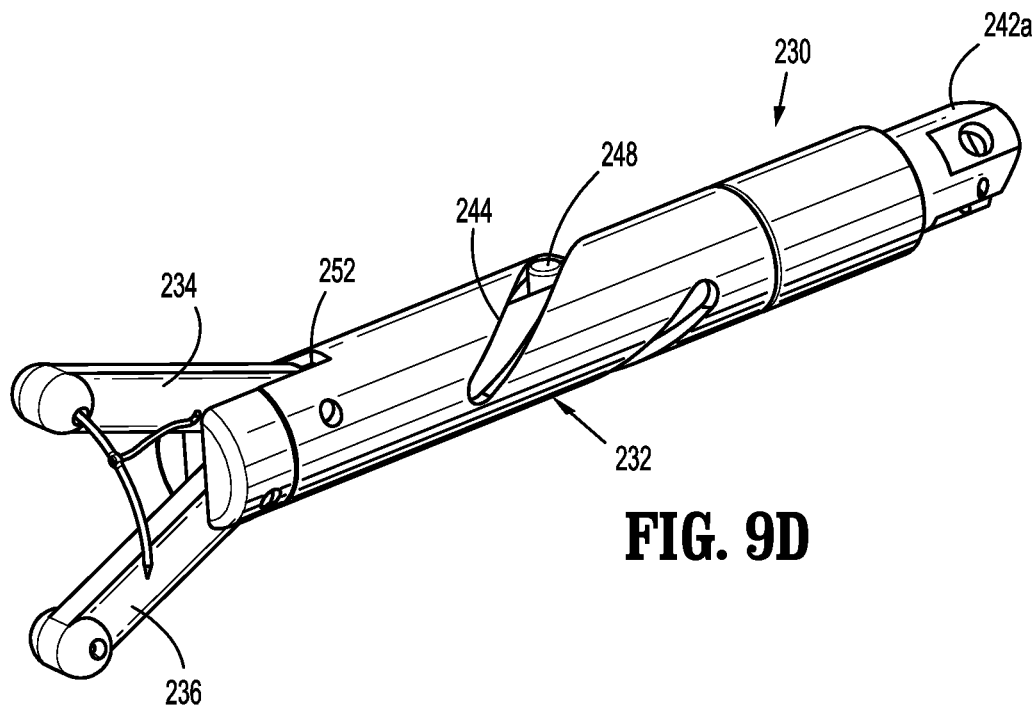
FIG. 9D is a perspective view of the end effector of FIG. 9A illustrating the jaw members after the first jaw member has been rotated in a second direction.
Figure 9E:
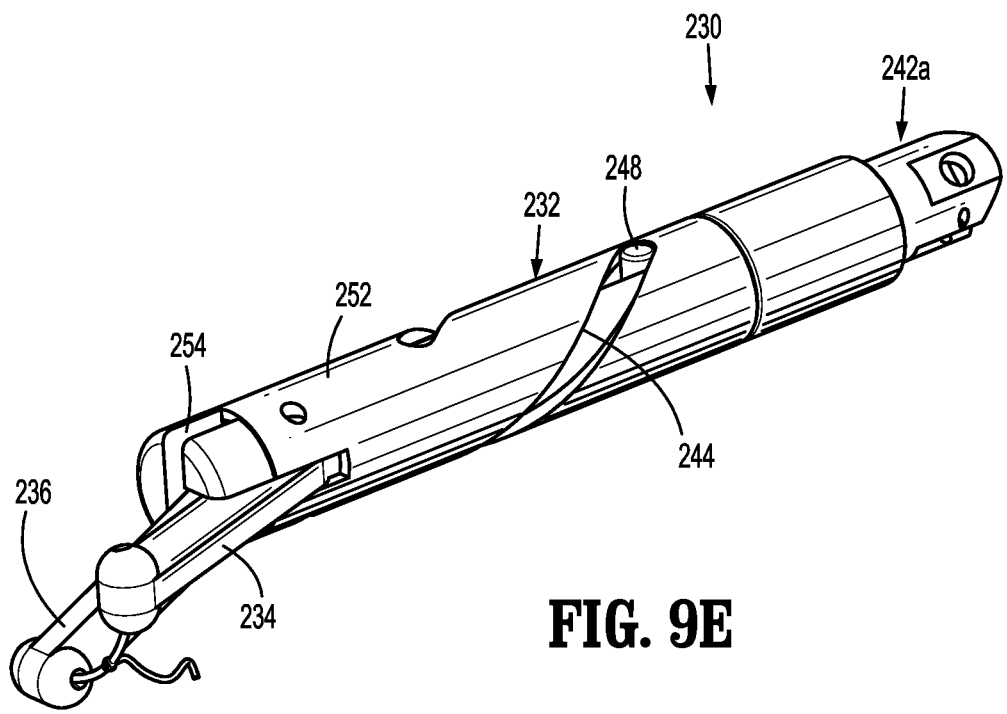
FIG. 9E is a perspective view of the end effector of FIG. 9A illustrating the jaw members engaged to opposite ends of a curved needle.
Figure 13:
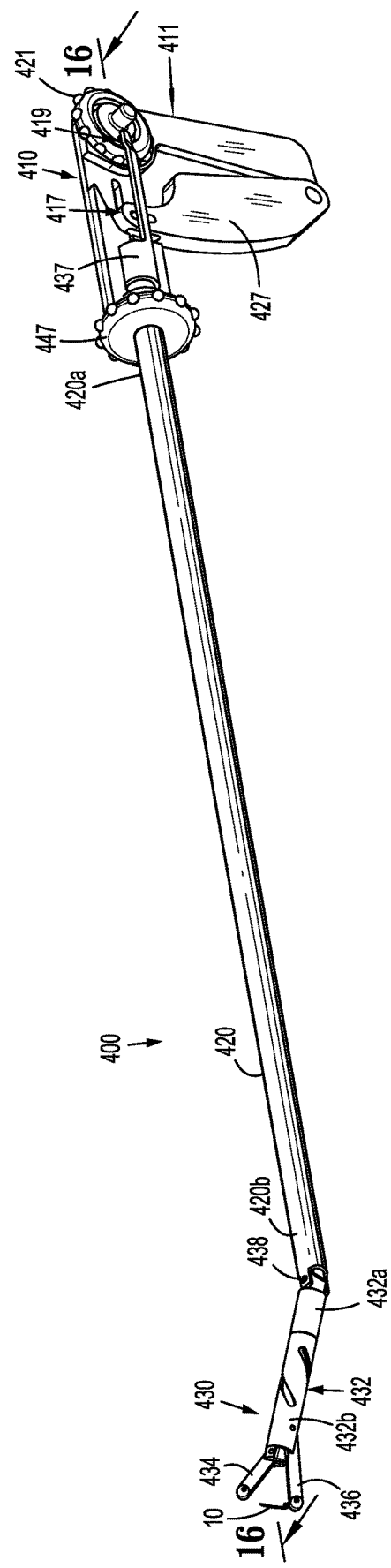
FIG. 13 is a perspective view of another embodiment of a surgical suturing instrument.
Figure 14:
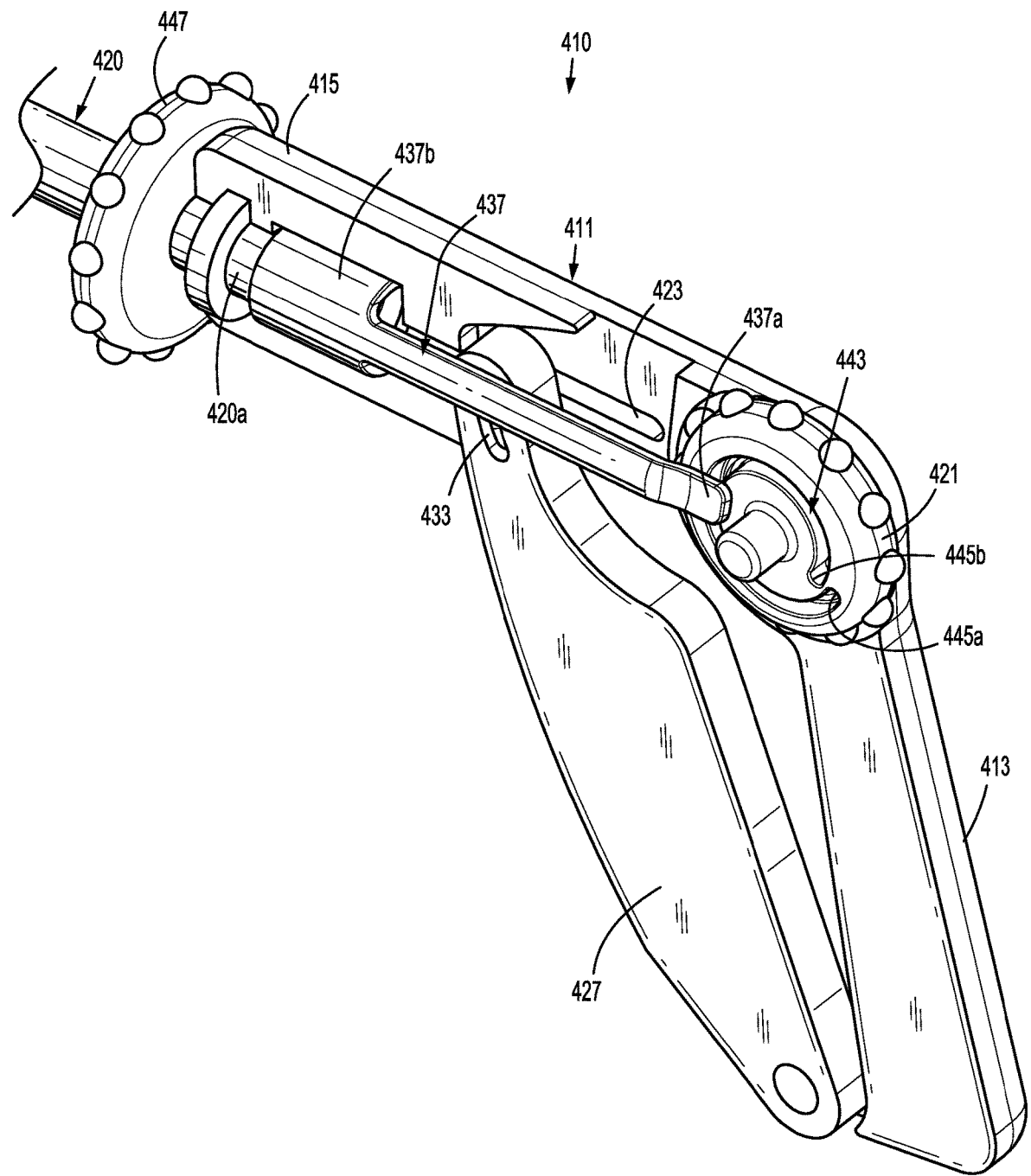
FIG. 14 is a perspective view, with parts removed, of a handle assembly of the surgical suturing instrument of FIG. 13.

The inner shaft 242 has a proximal portion 242a that is operably coupled to an actuation mechanism (not shown) of handle assembly 110. In this way, inner shaft 242 of end effector 230 may be longitudinally movable relative to outer shaft 240 in either a proximal or distal direction. It is contemplated that distal portion 242b of inner shaft 242 has ramped surfaces such that proximal movement of inner shaft 242 relative to first and second jaw members 234, 236 raises first and second jaw members 234, 236 from the first position, in which first jaw member 234 extends through slots 252, 254, to a second position, in which first and second jaw members 234, 236 are splayed outwardly relative to body portion 232, as shown in FIG. 9B. In some embodiments, end effector 230 may include any suitable mechanism capable of pivoting jaw members 234, 236 relative to one another. It is contemplated that end effector 230 includes a biasing element, for example, a spring, that resiliently biases jaw members 234, 236 toward the first, closed position.

A distal portion of each of the first and second jaw members 234, 236 defines a hole or aperture 256, 258 therein, similar to holes 156, 158 of jaw members 134, 136 described above. Holes 256, 248 extend entirely through a thickness of first and second jaw members 234, 236, respectively. In some embodiments, holes 256, 258 may only extend partially through a thickness of first and second jaw members 234, 236. Holes 256, 258 are configured to selectively retain an end of curved needle 10 therein such that needle 10 may be passed to and from first and second jaw members 234, 236 during a surgical procedure. This may be accomplished using any of the mechanisms described above, for example, push latches.

In operation, to perform a minimally invasive procedure involving suturing tissue, for example, a hernia repair, an access tube or cannula is positioned through surface tissue of a patient to gain access to a surgical site within a body of the patient. First and second jaw members 234, 236 of end effector 230 are moved to the closed configuration, in which first and second jaw members 234, 236 are parallel with longitudinal axis "X" of body portion 232 and are nested within slots 252, 254 of outer and inner shafts 240, 242 of body portion 232. With first and second jaw members 234, 236 in the closed configuration, end effector 230 is passed through the cannula to position jaw members 234, 236, with curved needle 10, adjacent the subject tissue. Inner shaft 242 of body portion 232 is moved proximally relative to outer shaft 240, thereby moving ramped surfaces (not shown) of inner shaft 242 proximally along first and second jaw members 234, 236 to pivot jaw members 234, 236 away from one another to the open configuration.

With jaw members 234, 236 in the open configuration and the distal portion of first jaw member 234 outside of slots 252 and 254 of each of the outer and inner shafts 240, 242 of body portion 232, the actuation bar 246 is moved in a distal direction through body portion 232. As the actuation bar 246 is moved distally, cam 248 moves distally through cam slot 244 of outer shaft 240 to drive a rotation of outer shaft 240 relative to inner shaft 242, in a direction indicated by arrow "E" in FIG. 9C. Since first jaw member 234 is coupled to outer shaft 240, first jaw member 234 is rotated with outer shaft 240 toward second jaw member 236 to drive needle 10 through tissue along a circular pathway around longitudinal axis "X" of body portion 232. Rotation of first jaw member 234 is continued until hole 258 of second jaw member 236 receives an opposite or second end of curved needle 10. Curved needle 10 is transferred from first jaw member 234 to second jaw member 236.

With curved needle 10 connected to second jaw member 236, the actuation bar 246 may be actuated to move the actuation bar 246 in a proximal direction through body portion 232 of end effector 230. Movement of the actuation bar 246 in a proximal direction proximally moves cam 248 through cam slot 244 of outer shaft 240 to drive a rotation of outer shaft 240, and in turn, first jaw member 236, away from second jaw member 236. This process may be continued until the subject tissue is sutured.

With reference to FIGS. 10A-12C, an end effector 330 of a surgical suturing instrument, similar to surgical suturing instrument 100 described above with reference to FIGS. 1-9E, is provided. End effector 330 is similar to either of the end effectors 130, 230 described above with reference to FIGS. 1-9E. Thus, end effector 330 will only be described in the detail necessary to elucidate particular differences between the embodiments. End effector 330 may be remotely operable by a handle assembly, for example, the handle assembly 110 of FIG. 1, or any other suitable actuating mechanism.

End effector 330 includes a body portion 332 and first and second jaw members 334, 336 pivotably coupled to body portion 332. A distal portion of each of the first and second jaw members 334, 336 defines a hole or aperture 356, 358 therein, similar to holes 156, 148 described above. Holes 356, 358 extend entirely through a thickness of first and second jaw members 334, 336. In some embodiments, holes 356, 358 may only extend partially through a thickness of first and second jaw members 334, 336. Holes 356, 358 are configured to selectively retain an end of a curved needle 10 therein such that needle 10 may be passed to and from first and second jaw members 334, 336 during a surgical procedure.

End effector 330 includes a cup member, such as, for example, a nest in the form of a ball-shaped element, pivotably disposed within hole 356 of first jaw member 334. It is contemplated that end effector 330 may include a second nest pivotably disposed within hole 358 of second jaw member 336. Nest is configured to hold an end of curved needle 10 therein and to pivot relative to first jaw member 334, thereby pivoting curved needle 10 relative to first jaw member 334. It is contemplated that end effector 330 may include an actuator rod (not shown) operably coupled to the handle assembly 110 (FIG. 1) and operably coupled to nest such that actuation of the actuator rod pivots the nest within hole 356 and relative to first jaw member 334.

In operation, to perform a minimally invasive procedure involving suturing tissue, for example, a hernia repair, an access tube or cannula is positioned through surface tissue of a patient to gain access to a surgical site within a body of the patient. First and second jaw members 334, 336 of end effector 330 are moved to the closed configuration, in which first and second jaw members 334, 336 are parallel with body portion 332. Nest of first jaw member 334 is manipulated so that curved needle 10 is disposed adjacent or in abutting engagement with jaw members 334, 336, as shown in FIGS. 10A and 10B. With curved needle 10 adjacent first jaw member 334, the overall profile of end effector 330 is reduced allowing end effector 330 to be passed through a smaller dimensioned cannula or access tube.

With first and second jaw members 334, 336 in the closed configuration and the curved needle 10 side-by-side with first jaw member 334, end effector 330 is passed through the cannula to position jaw members 334, 336, with curved needle 10, adjacent the subject tissue. Jaw members 334, 336 are pivoted away from one another to the open configuration in preparation for suturing tissue, as shown in FIGS. 11A and 11B.

With reference to FIGS. 12A-12C, with jaw members 334, 336 in the open configuration, the actuator rod of end effector 330 is actuated to rotate nest, thereby rotating curved needle 10 outwardly away from first jaw member 334, in the direction indicated by arrow "F" in FIG. 12B. Curved needle 10 is rotated via nest until an axis defined by curved needle 10 is aligned with holes 356, 358 of each of first and second jaw members 334, 336. In some embodiments, an ancillary surgical instrument, for example, a grasper, may be provided to manually rotate curved needle 10 outwardly relative to first jaw member 334. First jaw member 334 and/or second jaw member 336 may be rotated to drive needle 10 through tissue in a similar manner as that described above.

With reference to FIGS. 13-18C, another embodiment of a surgical suturing instrument is illustrated and identified generally as 400. Surgical suturing instrument 400 is similar to surgical suturing instrument 100 described above, and will therefore only be described with the detail necessary to elucidate particular differences therebetween. Surgical suturing instrument 400 includes a handle assembly 410, a shaft 420 extending distally from handle assembly 410, and an end effector 430 that extends from a distal portion 420b of shaft 420.

Handle assembly 410 of surgical suturing instrument 400 includes a handle housing 411 supporting an actuation assembly 417 and an articulation assembly 419. Handle housing 411 has a handle 413 and a barrel portion 415 extending substantially perpendicularly from handle 413. Handle 413 has an articulation wheel 421 of articulation assembly 419 rotatably supported therein. Barrel portion 414 of handle housing 411 has a longitudinally-extending slot 423 defined therein and a cavity 425 defined therein.

Actuation assembly 417 of handle assembly 410 includes a trigger 427, an actuation shaft 429, and a pin 429a attached to a proximal portion of actuation shaft 429. Slot 423 of barrel portion 415 has the pin 429a of actuation assembly 417 extending transversely therethrough. Pin 429 also extends within a vertically-oriented slot 433 defined in trigger 427 such that movement of trigger 427 relative to handle housing 411 moves pin 429a through slot 423 of barrel portion 415. Actuation shaft 429 of actuation assembly 417 extends perpendicularly from pin 429a, through cavity 425 of barrel portion 415, and terminates in a distal portion 429b that is operably coupled to end effector 430 in a manner to rotate jaw members 434, 436 of the end effector 430 upon actuation of trigger 427, as will be described in detail below.

Articulation assembly 419 of handle assembly 410 includes an elongate member 437, an articulation bar 439 extending distally from the elongate member 437, and the articulation wheel 421, which is rotatably supported in handle 413 of handle housing 411. The elongate member 437 of articulation assembly 419 has a proximal portion 437a and a tubular distal portion 437b. The proximal portion 437a of the elongate member 437 has a pin 441 extending therefrom that is received in a channel 443 defined in articulation wheel 421. Channel 443 of articulation wheel 421 spirals radially inward/outward about a rotation axis of articulation wheel 421 and has two opposite ends defined by two opposite end walls 445a, 445b. Pin 441 of elongate member 437 is disposed a radial distance away from the axis about which articulation wheel 421 rotates. In some embodiments, pin 441 of elongate member 437 may be disposed above/below the axis about which articulation wheel 421 rotates. In operation, a rotation of articulation wheel 421 brings one of the end walls 445a, 445b of channel 443 of articulation wheel 421 into engagement with pin 441 of elongate member 437 to drive one of a proximal or distal movement of elongate member 437 through barrel portion 415 of handle housing 111.

Figure 15:
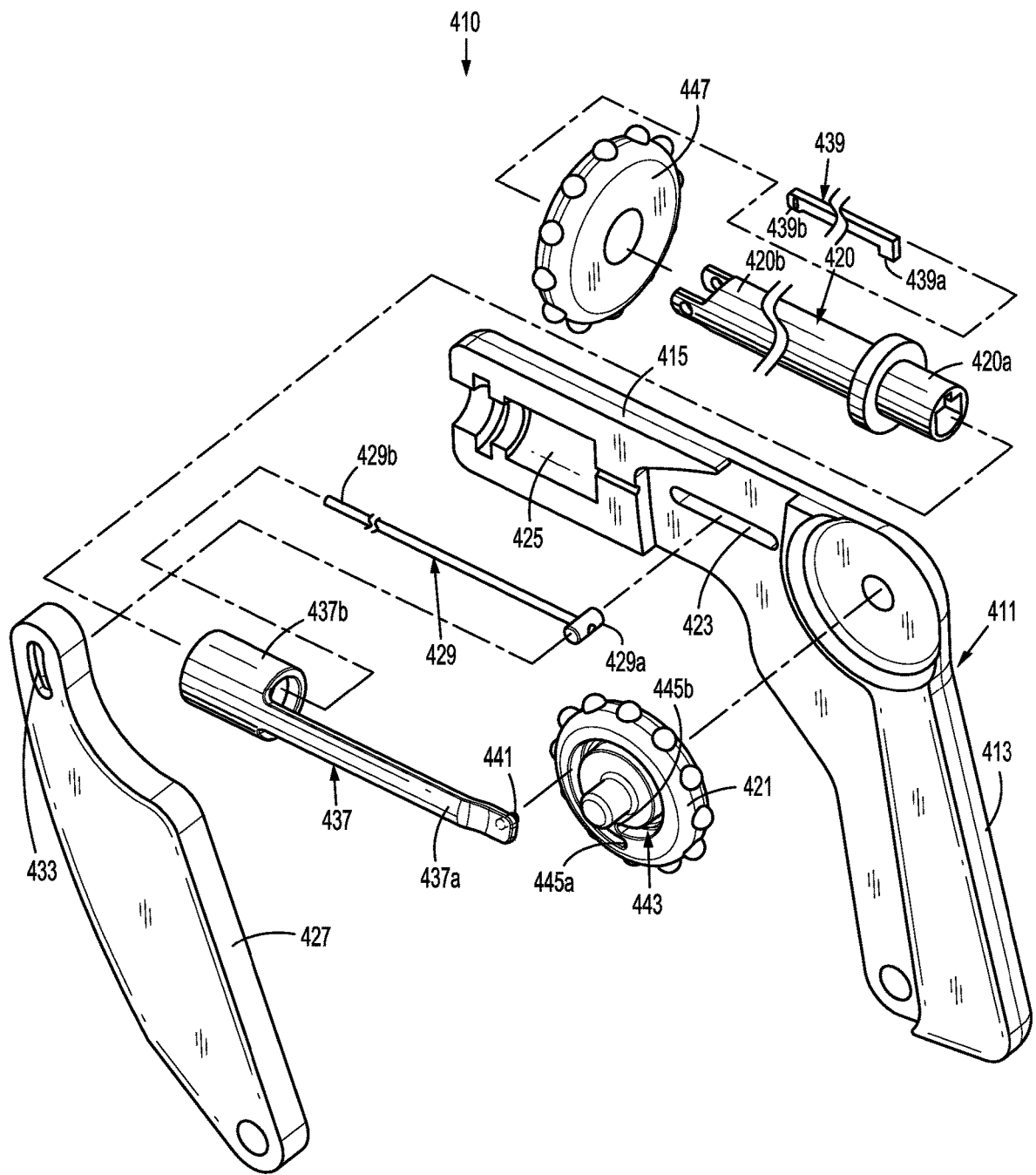
FIG. 15 is a perspective view, with parts separated, of the handle assembly of FIG. 14.
Figure 16:
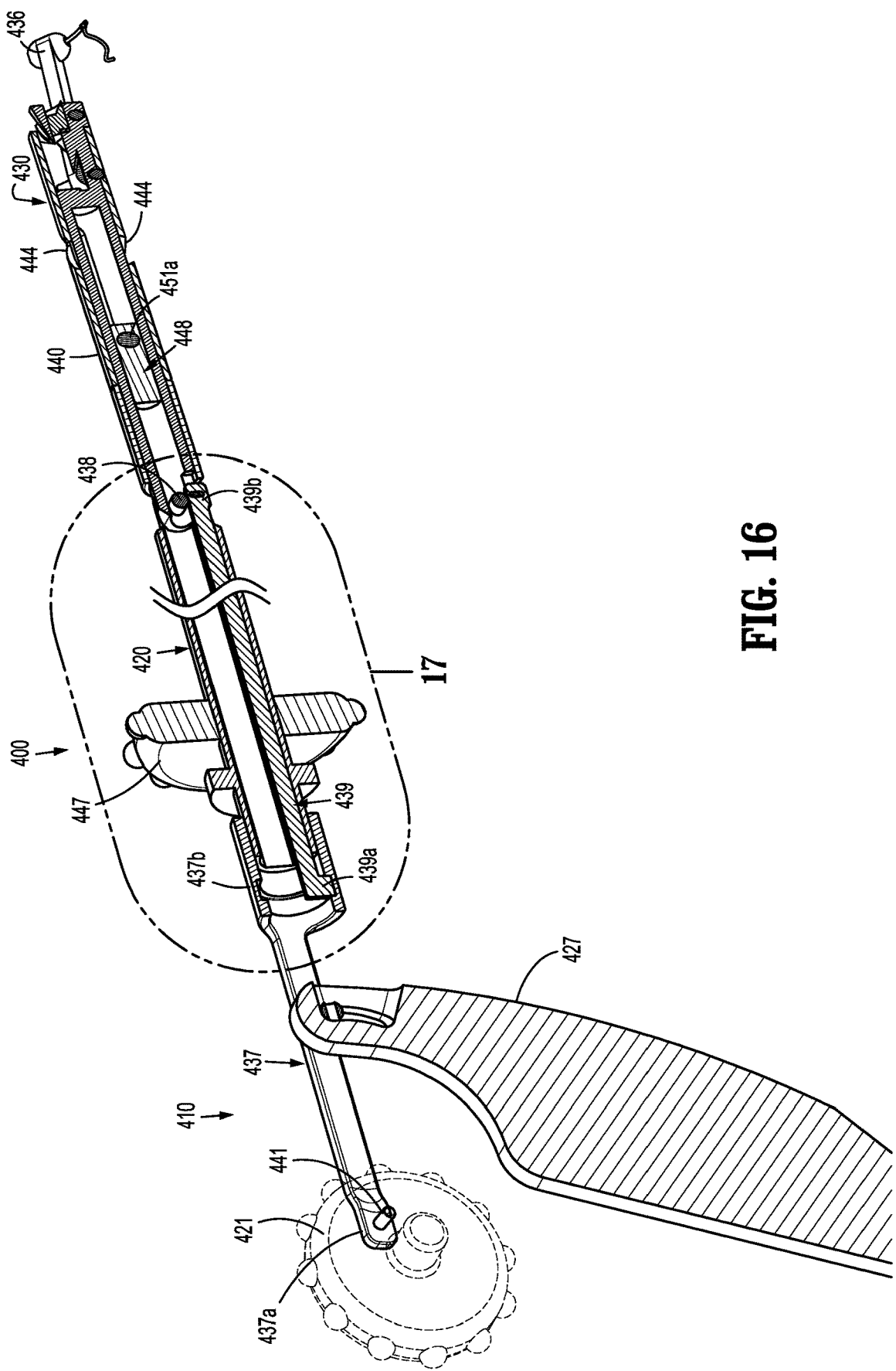
FIG. 16 is a cross-sectional view, taken along line 16-16 of FIG. 13, with parts removed, of the surgical suturing instrument.
Figure 17:
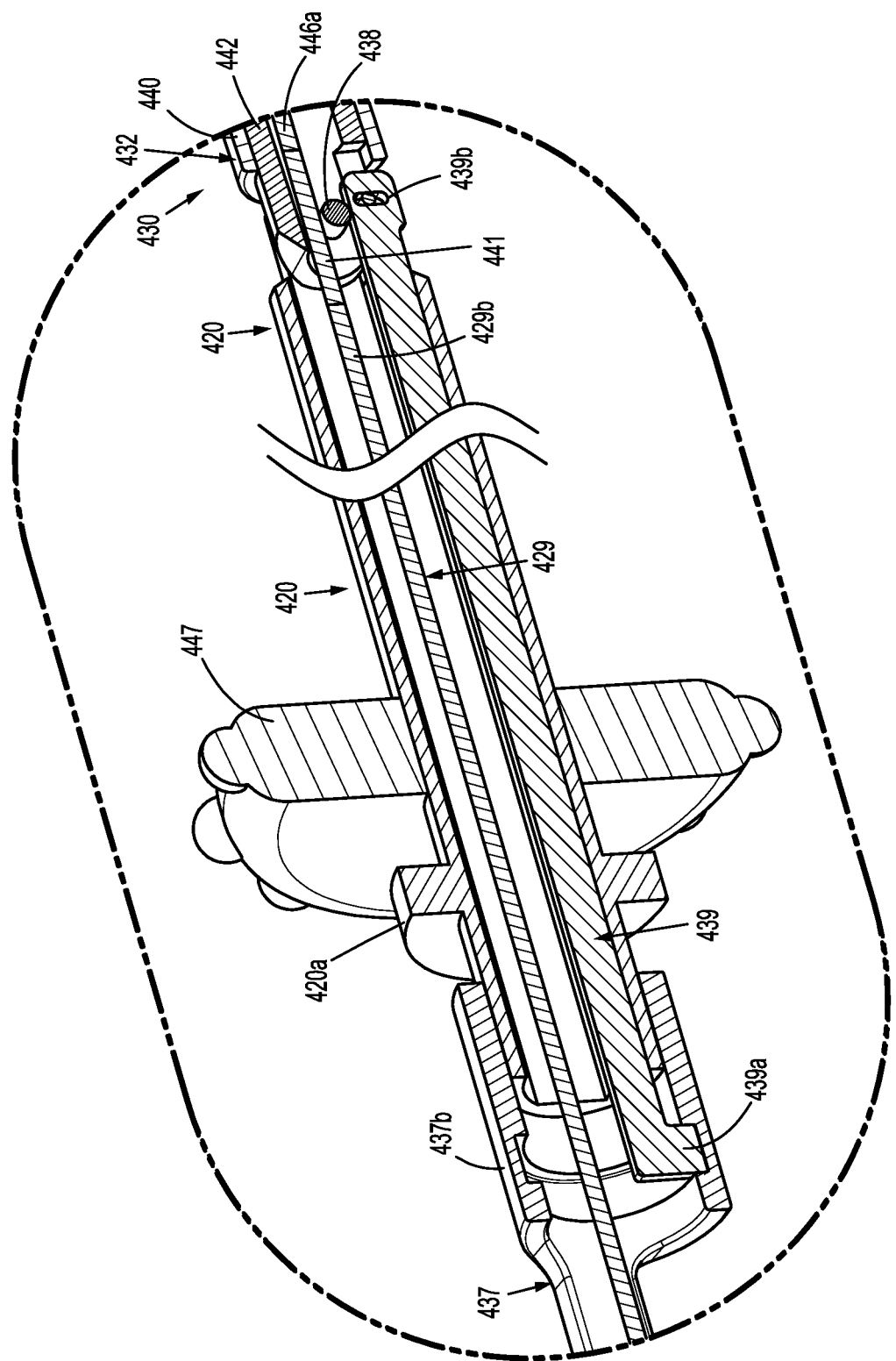
FIG. 17 is an enlarged view of detail 17 shown in FIG. 16 with an actuation shaft added.

With reference to FIGS. 15-17, articulation shaft 439 of articulation assembly 419 has a proximal portion 439a disposed within tubular distal portion 437b of elongate member 437 and is fixed to an inner surface thereof such that articulation shaft 439 moves with elongate member 437. Articulation shaft 439 of articulation assembly 419 has a distal portion 439b operably coupled to end effector 430 at a location adjacent an articulation joint, for example, an articulation pin 438. In particular, articulation shaft 439 of articulation assembly 419 is spaced radially outward of articulation pin 438 (i.e., offset from a central longitudinal axis of shaft 420) such that longitudinal movement of articulation shaft 439, via rotation of rotation wheel 421, effects an articulation of end effector 430 relative to shaft 420 about articulation pin 438 in one of two opposing directions.

Handle assembly 410 further includes a rotation wheel 447 disposed about and rotationally fixed to shaft 420 of surgical suturing instrument 400. In this way, shaft 420 of surgical suturing instrument 400 rotates about its longitudinal axis in response to a rotation of rotation wheel 447. Shaft 420 of surgical suturing instrument 400 has a proximal portion 420a disposed within cavity 425 of handle housing 411 and a distal portion 420b. End effector 400 of surgical suturing instrument 400 is pivotably coupled to distal portion 420b of shaft 420.

With reference to FIGS. 17 and 18A-18C, end effector 430 generally includes an elongated body portion 432 and first and second jaw members 434, 436 each pivotably coupled to body portion 432 of end effector 430. In some embodiments, jaw members 434, 436 may be non-pivotable in relation to body portion 432 or, in other embodiments, only one of jaw members 434, 436 may be pivotable in relation to body portion 432. Body portion 432 has a proximal portion pivotably coupled to distal portion 420b of shaft 420 of surgical suturing instrument 400 via the articulation pin 438 mentioned above. As such, end effector 430 is articulatable relative to shaft 420 about the articulation pin 438 via the articulation assembly 419 (FIG. 13) described above.

Body portion 432 of end effector 420 includes a rotatable outer shaft 440 and an inner shaft 442 non-rotatably disposed within outer shaft 440. Outer shaft 440 has first jaw member 434 coupled to a distal portion thereof, and inner shaft 442 has second jaw member 436 coupled to a distal portion thereof, such that first jaw member 434 rotates relative to second jaw member 436 with a rotation of outer shaft 440. Outer shaft 440 of body portion 432 defines a helical cam slot 444 formed therein. In some embodiments, cam slot 444 may assume a variety of patterns, for example, zig-zag, undulating, or the like. End effector 430 includes an actuation bar 446 that is configured to translate along a longitudinal axis of body portion 432 in response to an actuation of trigger 427 of handle assembly 410.

In particular, actuation bar 446 has a proximal portion 446a (FIG. 17) coupled to distal portion 429b of actuation rod 429 of handle assembly 410. In some embodiments, actuation shaft 429 of handle assembly 410 and actuation bar 446 of end effector 430 are integrally formed with one another. Actuation shaft 429 of handle assembly 410 is coupled to actuation bar 446 via a flexible elongate member 449 disposed at a location adjacent articulation pin 438 of shaft 420 so that as end effector 430 articulates relative to shaft 420, actuation bar 446 bends relative to actuation shaft 429 about flexible elongate member 449. In some embodiments, actuation shaft 429 and actuation bar 446 are each formed from a flexible material permitting actuation bar 446 to flex relative to actuation shaft 429 during articulation of end effector 430.

Actuation bar 446 has a distal portion 446b having a projection or cam 448 that is slidably received within cam slot 444 of outer shaft 440. Upon the axial translation of actuation mechanism 446 relative to body portion 432, projection 448 moves through cam slot 444 of outer shaft 440 to rotate outer shaft 440 about the longitudinal axis of body portion 432 and, in turn, rotate first jaw member 434.

Inner shaft 442 of body portion 432 is pivotably coupled to distal portion 420b of shaft 420 via a joint, for example, the articulation pin 438, while being non-rotatable relative to shaft 420 about longitudinal axis of shaft 420. Jaw member 436 is pivotably coupled to a distal portion of inner shaft 442. In this way, inner shaft 442 renders end effector 430 articulatable relative to shaft 420 while preventing jaw member 434 from rotation relative to inner shaft 442 about the longitudinal axis of body portion 432. Inner shaft 442 of body portion 432 defines a longitudinally-extending slot 450 having cam 448 of actuation bar 446 extending therethrough. Slot 450 of inner shaft 442 acts to guide cam 448 in a straight line through body portion 432.

Figure 18A:
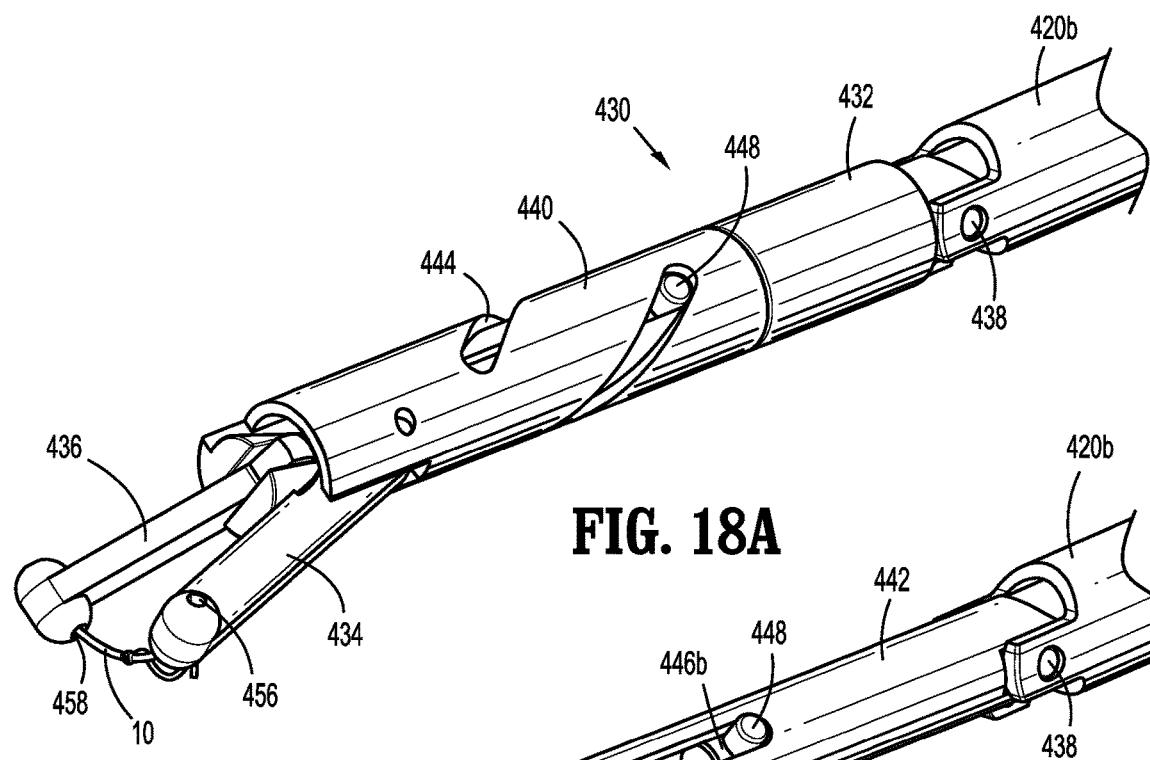
FIG. 18A is a perspective view of the end effector of the surgical suturing instrument of FIG. 13.
Figure 18B:
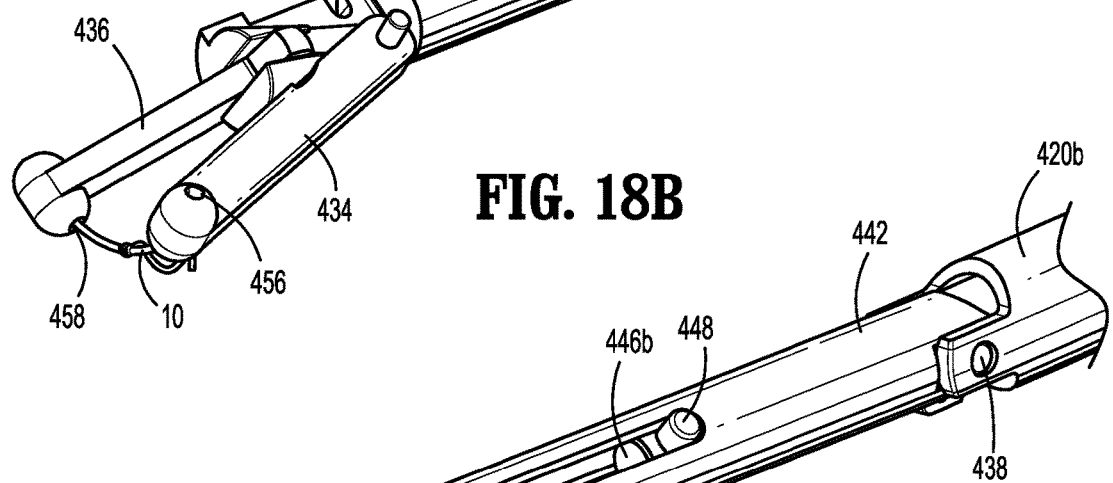
FIG. 18B is a perspective view, with parts removed, of the end effector of FIG. 18A.
Figure 18C:
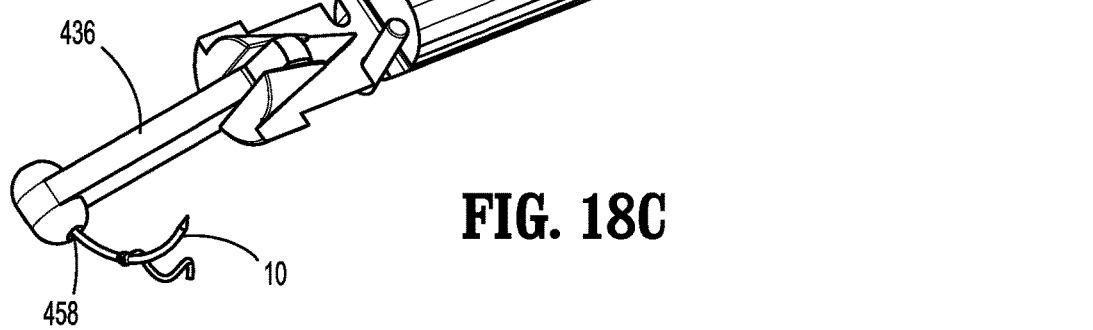
FIG. 18C is a perspective view, with parts removed, of the end effector shown in FIG. 18B.

With continued reference to FIGS. 18A-18C, a distal portion of each of the first and second jaw members 434, 436 defines a hole or aperture 456, 458 therein, similar to holes 156, 158 described above. Holes 456, 448 extend entirely through a thickness of first and second jaw members 434, 436, respectively. In some embodiments, holes 456, 458 may only extend partially through a thickness of first and second jaw members 434, 436. Holes 456, 458 are configured to selectively retain an end of curved needle 10 therein such that needle 10 may be passed to and from first and second jaw members 434, 436 during a surgical procedure. This may be accomplished using any of the mechanisms described above, for example, push latches.

In operation, to perform a minimally invasive procedure involving suturing tissue, for example, a hernia repair, an access tube or cannula is positioned through surface tissue of a patient to gain access to a surgical site within a body of the patient. End effector 430 is passed through the cannula to position jaw members 434, 436, with curved needle 10, adjacent the subject tissue. The actuation bar 446 of end effector 430 is moved in a distal direction through body portion 232 in response to an actuation of trigger 427. As the actuation bar 446 is moved distally, cam 448 moves distally through cam slot 444 of outer shaft 440 to drive a rotation of outer shaft 440 relative to inner shaft 442. Since first jaw member 434 is coupled to outer shaft 440, first jaw member 434 is rotated with outer shaft 440 toward second jaw member 436 to drive needle 10 through tissue along a circular pathway around the longitudinal axis of body portion 432. Rotation of first jaw member 434 is continued until hole 458 of second jaw member 436 receives an end of curved needle 10 to transfer curved needle 10 from first jaw member 434 to second jaw member 436.

With curved needle 10 connected to second jaw member 436, the actuation bar 446 may be actuated to move the actuation bar 446 in a proximal direction through body portion 432 of end effector 430. Movement of the actuation bar 446 in a proximal direction moves cam 448 in the proximal direction through cam slot 444 of outer shaft 440 to drive a rotation of outer shaft 440, and in turn, first jaw member 436, away from second jaw member 436. This process may be continued until the subject tissue is sutured.

The surgical suturing instruments, or end effectors thereof, described herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the surgical suturing instruments, or component thereof, disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 19:
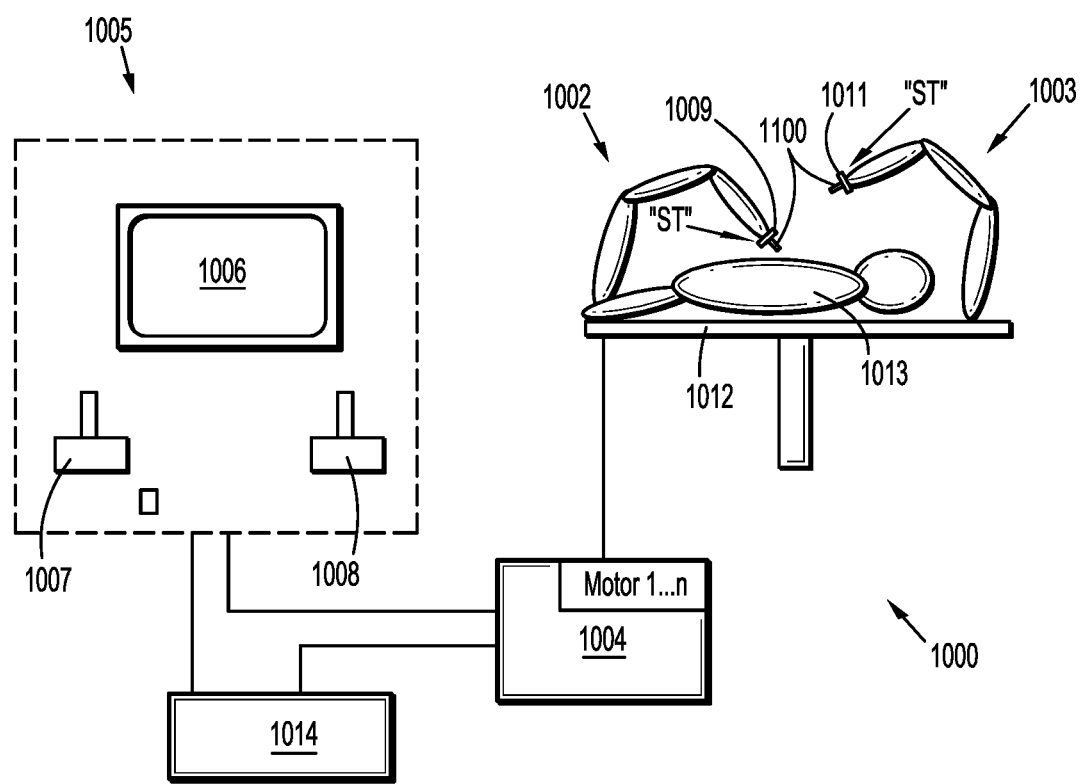
FIG. 19 is a schematic illustration of a robotic surgical system configured for use in accordance with the disclosure.
Figure 20:
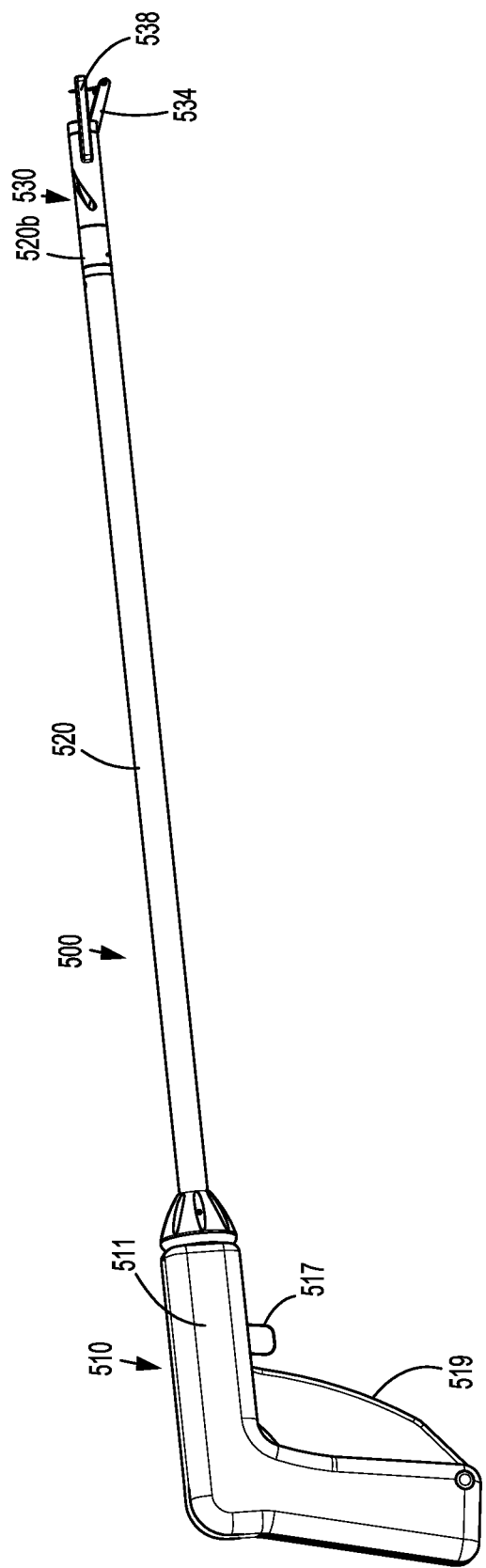
FIG. 20 is a side view illustrating another embodiment of a surgical suturing instrument.
Figure 23:
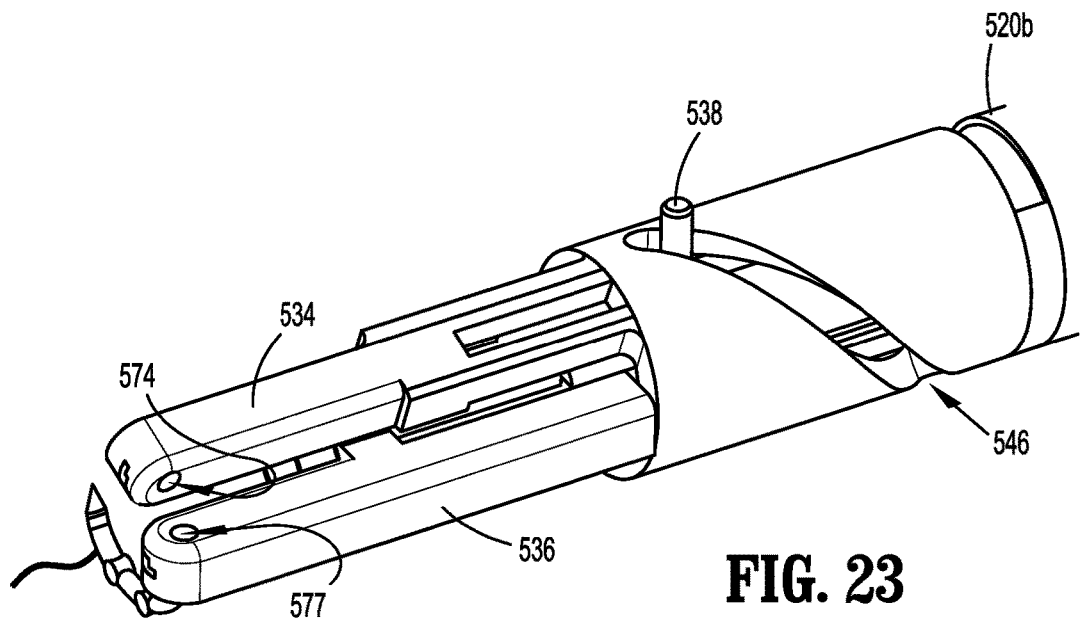
FIG. 23 is a side perspective view illustrating the jaw members of FIG. 21 in a separated state.
Figure 24:
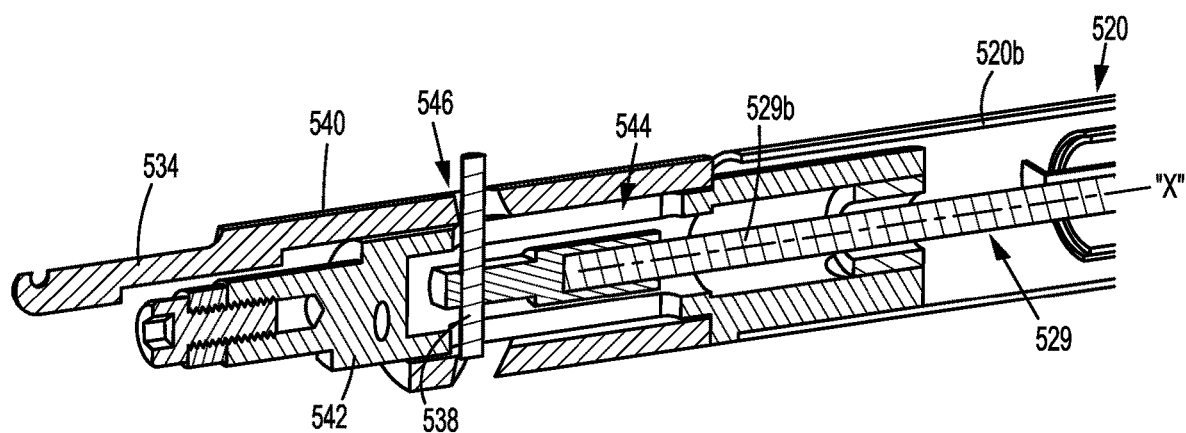
FIG. 24 is a side, cross-sectional view illustrating an actuation bar for moving the end effector between the approximated and separated states.
Figure 25:
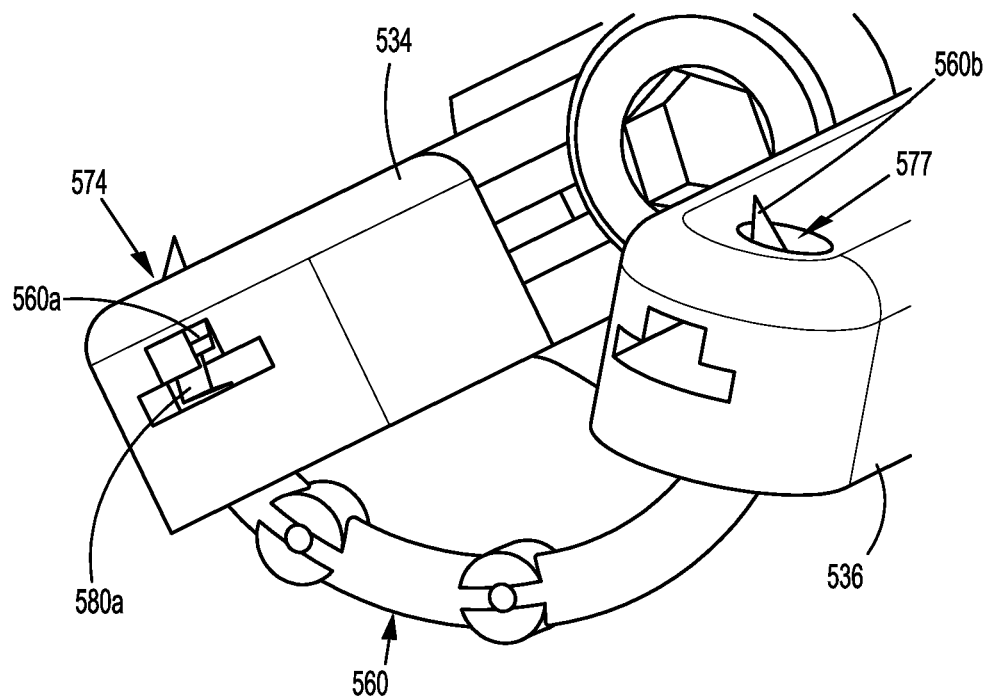
FIG. 25 is an enlarged perspective view illustrating the first and second jaw members of FIG. 21 transferring the curved needle therebetween.
Figure 26:
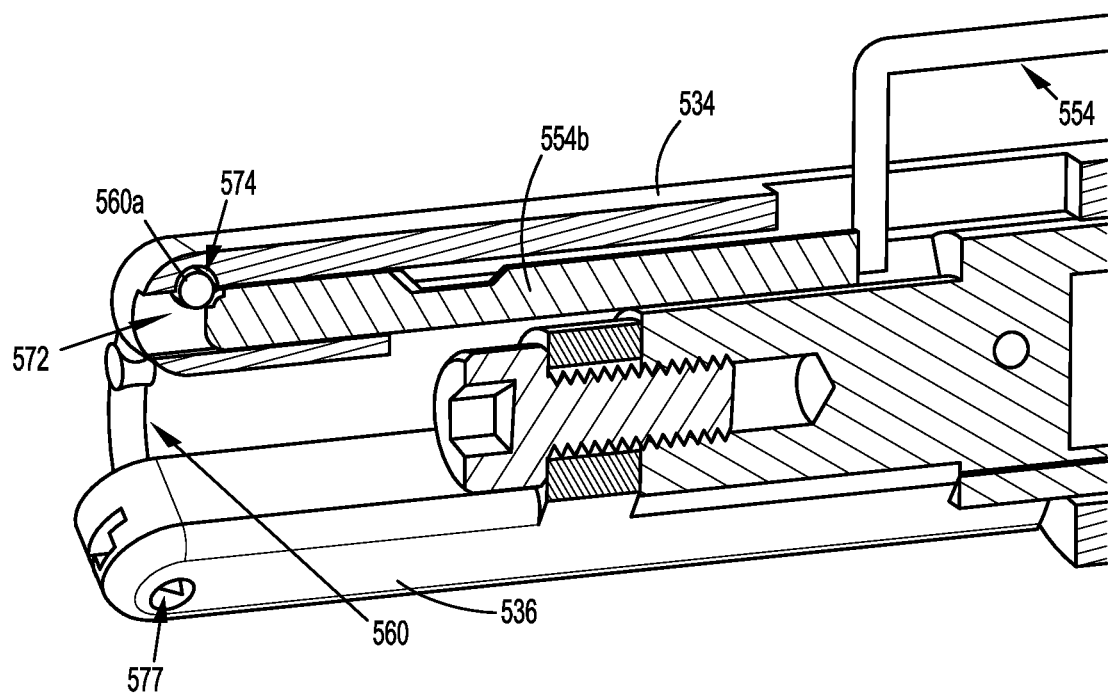
FIG. 26 is a side, cross-sectional view illustrating a first elongate locking element locking the curved needle to the first jaw member of FIG. 21.
Figure 27:
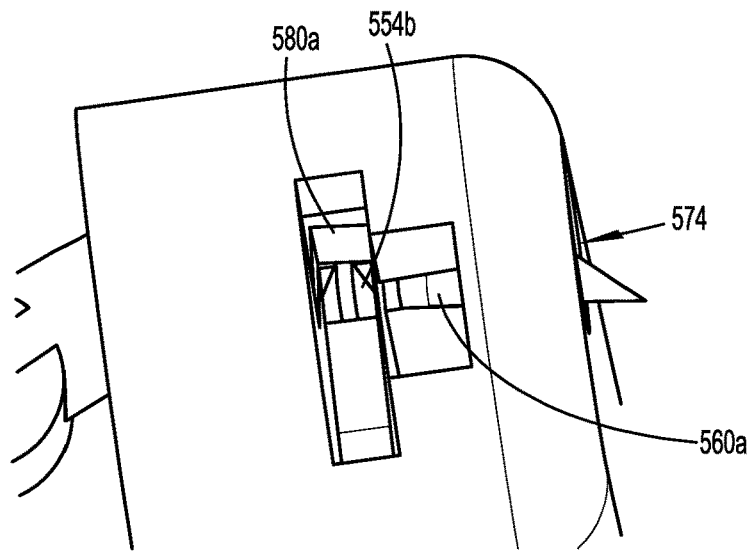
FIG. 27 is an enlarged view illustrating the first elongate locking element of FIG. 26 locking the curved needle to the first jaw member.
Figure 28:
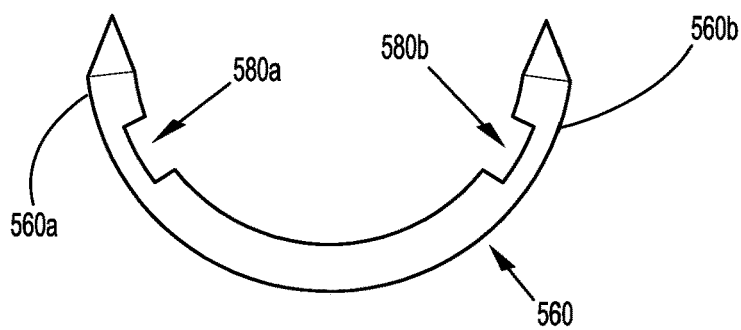
FIG. 28 is a plan view of the curved needle of FIG. 22.

With reference to FIG. 19, one exemplary robotic surgical system or medical workstation 1000 may generally include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments of end effectors 130, 230, 330, or 430 disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

With reference to FIGS. 20-29, another embodiment of a surgical suturing instrument 500 is illustrated. Surgical suturing instrument 500 is similar to surgical suturing instrument 100 described above, and will therefore only be described with the detail necessary to elucidate particular differences therebetween. Surgical suturing instrument 500 generally includes a handle assembly 510, a shaft 520 extending distally from handle assembly 510, and an end effector 530 that extends from a distal end portion 520*b* of shaft 520. Handle assembly 510 of surgical suturing instrument 500 includes a handle housing 511 supporting a first trigger 517 and a second trigger 519.

With reference to FIGS. 20-24, surgical suturing instrument 500 includes an actuation bar 529 having a proximal end portion 529*a* operably coupled to the second trigger 519. Actuation bar 529 terminates in a distal end portion 529*b* that is operably coupled to end effector 530 in a manner to rotate a first jaw member 534 of end effector 530 upon actuation of second trigger 519, as will be described in detail below. The actuation bar 529 has a drive pin 538 extending perpendicularly through distal end portion 529*b* thereof. Drive pin 538 is configured to rotate first jaw member 534 about a longitudinal axis "X" defined by shaft 520.

End effector 530 has a tubular outer body portion 540 and an inner body portion 542 disposed within outer body portion 540. Inner body portion 542 of end effector 530 extends distally from distal end portion 520*b* of shaft 520 and is rotationally fixed relative to shaft 520. Inner body portion 542 of end effector 530 defines a longitudinally-extending slot 544 (FIG. 24) through which drive pin 538 of actuation bar 529 extends. An actuation of second trigger 519 is configured to advance drive pin 538 of actuation bar 529 through slot 544 of inner body portion 542. Outer body portion 540 of end effector 530 is rotationally supported on inner body portion 542 and defines a helical cam slot 546 through which drive pin 538 of actuation bar 529 extends. Since first jaw member 534 of end effector 530 is fixed to outer body portion 540, advancement of drive pin 538 through helical cam slot 546 of outer body portion 540 drives a rotation of first jaw member 534 about longitudinal axis "X."

Surgical suturing instrument 500 includes first and second push rods 548, 550, a bearing assembly 552, and first and second elongate locking elements 554, 556 cooperatively functioning to selectively lock a suture needle, such as, for example, a curved needle 560, to one of the first or second jaw members 534, 536. First and second push rods 548, 550 each have a proximal end portion 558, 562 operably coupled to first trigger 517 of handle assembly 510. First and second push rods 548, 550 are configured to translate (e.g., move distally and proximally) in a direction parallel with the longitudinal axis "X" of shaft 520 in response to an actuation of first trigger 517. In some aspects, first and second push rods 548, 550 may be operably coupled to distinct triggers (e.g., triggers 517 and 519 respectively). First trigger 517 is configured to simultaneously translate push rods 548, 550 in opposite directions.

Bearing assembly 552 includes an outer race 564 and an inner race 566 rotationally supported in the outer race 564. A distal end portion 568 of first push rod 548 is fixed (e.g., via an adhesive or any suitable fastener) to the inner race 566 of bearing assembly 552. In some embodiments, distal end portion 568 of first push rod 548 is fixed to outer race 564 of bearing assembly 552 instead of inner race 566. Due to first push rod 548 being coupled to bearing assembly 552, both inner and outer races 566, 564 of bearing assembly 552 move distally with first push rod 548.

The first elongate locking element 554 may have a rod-shape and extends between a proximal end portion 554a and a distal end portion 554b. The proximal end portion 554a of first elongate locking element 554 is coupled to outer race 564 of bearing assembly 552. In other aspects, proximal end portion 554a of first elongate locking element 554 may be coupled to inner race 566 of bearing assembly 552 rather than outer race 564. Proximal end portion 554a of first elongate locking element 554 has a connector 570 extending therefrom fixed to outer race 564, such that as outer race 564 rotates relative to inner race 566, first elongate locking element 554 rotates therewith. Distal end portion 554b of first elongate locking element 554 may have a substantially flattened, blade-like shape. Second elongate locking element 556 is coupled to second push rod 550.

The first trigger 517 is configured to simultaneously translate the first and second elongate locking elements 554, 556 in opposite directions. For example, an initial actuation of first trigger 517 may cause first elongate locking element 554 to advance and second elongate locking element 556 to retract.

First jaw member 534 is monolithically formed with outer body portion 540. In some aspects, first jaw member 534 may be connected to outer body portion 540. Second jaw member 536 is fixed relative to inner body portion 542. Due to the similarities between first and second jaw members 534, 536, only details with respect to first jaw member 534 will be further described herein.

First jaw member 534 and outer body portion 540 of end effector 530 each define a coextensive, longitudinally-extending groove 572 in which first elongate locking element 554 is slidably supported. Distal end portion 554b of first elongate locking element 554 is captured in groove 572, such that first elongate locking element 554 rotates with first jaw member 534, whereby outer race 564 of bearing assembly 552 is also caused to rotate. Due to proximal end portion 554a of first elongate locking element 554 being coupled to bearing assembly 552, first elongate locking element 554 is configured to translate relative to and within first jaw member 534 without inhibiting rotation of first jaw member 534.

First jaw member 534 has a distal end portion (e.g., a distal tip) defining a hole 574 therein in communication with groove 572. Hole 574 extends at a perpendicular angle relative to groove 572 and is configured for detachable receipt of a first end 560a of curved needle 560. When the first end 560a of curved needle 560 is received in hole 574, first end 560a of curved needle 560 extends into groove 572 and into longitudinal alignment with distal end portion 554b of first elongate locking element 554.

With reference to FIGS. 25-28, first end 560a of curved needle 560 defines a first notch 580a therein configured to receive distal end portion 554b of first elongate locking element 554. Second end 560b of curved needle 560 defines a second notch 580b therein configured for removable receipt of a distal end portion of second elongate locking element 556. In some aspects, the notches 580a, 580b may be formed at any suitable location of curved needle 560.

Figure 29:
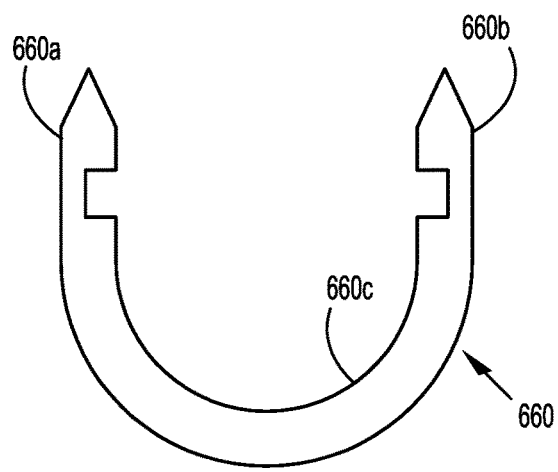
FIG. 29 is a plan view of another embodiment of a curved needle.

FIG. 29 illustrates another embodiment of a curved needle 660, similar to curved needle 560. Instead of having a continuous curvature along its length, curved needle 660 has first and second linear ends 660a, 660b interconnected via a curved intermediate segment 660c.

In operation, second end 560b of curved needle 560 is received in a hole 577 of second jaw member 536 and the distal end portion of second elongate locking element 556 is disposed within second notch 580b in curved needle 560. Therefore, in this condition, curved needle 560 is fixed to second jaw member 536. To pass curved needle 560 from second jaw member 536 to first jaw member 534, second trigger 519 may be actuated, whereby actuation bar 529 is moved distally through shaft 520. Drive pin 538 of actuation bar 529 moves through helical cam slot 546 of outer body portion 540 of end effector 530 to rotate outer body portion 540 and the attached first jaw member 534 about longitudinal axis "X" toward an approximated position with second jaw member 536.

Upon the first jaw member 534 entering the approximated position, first end 560a of curved needle 560 enters hole 574 in first jaw member 534, thereby aligning first notch 580a of curved needle 560 with grove 572 in first jaw member 534. With first end 560a of curved needle 560 in hole 574 of first jaw member 534, first trigger 517 may be actuated to simultaneously advance first push rod 548 and retract second push rod 550. Advancing first push rod 548 advances bearing assembly 552 and the attached first elongate locking element 554 from a proximal, non-locking position to a distal, locking position. In the proximal position, distal end portion 554b of first elongate locking element 554 is disposed proximally and out of hole 574 of the first jaw member 534, whereas in the distal position, distal end portion 554b of first elongate locking element 554 is disposed within hole 574 of the first jaw member 534. With first end 560a of curved needle 560 disposed in hole 574, advancement of the distal end portion 554b of the first elongate locking element 554 moves distal end portion 554b thereof into first notch 580a of first end 560a of curved needle 560, thereby locking first end 560a of curved needle 560 to first jaw member 534.

Since second push rod 550 concurrently retracts with the advancement of first push rod 548, second push rod 550 retracts the attached second elongate locking element 556 out of hole 577 in second jaw member 536 at the same time that distal end portion 554b of first elongate locking element 554 enters hole 574 in first jaw member 534. Therefore, the second elongate locking element 556 exits the second notch 580b in the second end 560b of curved needle 560 to release second end 560b of curved needle 560 from second jaw member 536, allowing curved needle 560 to transfer to first jaw member 534.

In embodiments, the first and second elongate locking elements 554, 556 and the actuation bar 529 may be actuated by the same trigger, such as, for example, first trigger 517 or second trigger 519. In such an embodiment, the actuation of the first and second elongate locking elements 554, 556 is timed so that it occurs immediately after first jaw member 534 is approximated towards second jaw member 536.

It will be understood that various modifications may be made to the embodiments disclosed herein. Therefore, the above description should not be construed as limiting, but merely exemplifications of embodiments. Those skilled in the art will envision other modification within the scope and spirit of the claims appended thereto.

The invention claimed is:

1. A surgical suturing instrument, comprising:
   a handle assembly;
   a shaft extending distally from the handle assembly and defining a longitudinal axis;
   an end effector including:
   a first jaw member coupled to a distal end portion of the shaft, the first jaw member defining a hole and a longitudinally-extending groove in communication with the hole, the hole configured for detachable receipt of a curved needle; and
   a second jaw member coupled to a distal end portion of the shaft and defining a hole configured for detachable receipt of the curved needle; and
   a first elongate locking element having a distal end portion slidably received in the groove, wherein the first elongate locking element is configured to move between a proximal, non-locking position in which the distal end portion of the first elongate locking element is disposed proximally of the hole of the first jaw member, and a distal, locking position in which the distal end portion of the first elongate locking element is disposed within the hole of the first jaw member for locking the curved needle to the first jaw member, wherein the first jaw member is configured to rotate relative to the second jaw member and the shaft about the longitudinal axis of the shaft.

2. The surgical suturing instrument according to claim 1, wherein the second jaw member defines a longitudinally-extending groove in communication with the hole of the second jaw member.

3. The surgical suturing instrument according to claim 2, further comprising a second elongate locking element having a distal end portion slidably received in the groove of the second jaw member, wherein the second elongate locking element is configured to move between:
   a proximal, non-locking position in which the distal end portion of the second elongate locking element is disposed proximally of the hole of the second jaw member for releasing the curved needle; and
   a distal, locking position in which the distal end portion of the second elongate locking element is disposed within the hole of the second jaw member for locking the curved needle to the second jaw member.

4. The surgical suturing instrument according to claim 1, wherein the hole of the first jaw member defines an axis that is perpendicular to an axis defined by the groove.

5. The surgical suturing instrument according to claim 1, further comprising a curved needle, wherein the curved needle is configured for detachable receipt in the hole of each of the first and second jaw members.

6. The surgical suturing instrument according to claim 5, wherein the curved needle has a first end defining a first notch configured for receiving the distal end portion of the first elongate locking element when the first end is in the hole of the first jaw member.

7. The surgical suturing instrument according to claim 6, wherein the curved needle has a second end defining a second notch.

8. The surgical suturing instrument according to claim 1, further comprising a bearing assembly including:
   an outer race; and
   an inner race supported in the outer race, wherein the first elongate locking element has a proximal end portion coupled to the outer race or the inner race.

9. The surgical suturing instrument according to claim 8, further comprising a push rod coupled to the other of the outer race or the inner race for moving the bearing assembly and the first elongate locking element between the proximal and distal positions.

10. The surgical suturing instrument according to claim 1, wherein the end effector includes an outer body portion rotationally coupled to the distal end portion of the shaft, the first jaw member fixed to and extending from the outer body portion.

11. The surgical suturing instrument according to claim 10, wherein the end effector includes an inner body portion disposed within the outer body portion, the second jaw member coupled to a distal end portion of the inner body portion.

12. The surgical suturing instrument according to claim 11, further comprising an actuation bar operably coupled to the handle assembly and configured to translate within the shaft in response to an actuation of the handle assembly, wherein the outer body portion defines a cam slot having a portion of the actuation bar received therein such that translation of the actuation bar rotates the outer body portion and the first jaw member relative to the inner body portion and the second jaw member.

13. A surgical suturing instrument, comprising:
    a handle assembly including a first trigger;
    a shaft extending distally from the handle assembly and defining a longitudinal axis;
    an end effector including:
    a tubular outer body portion rotatably coupled to a distal end portion of the shaft;
    a first jaw member extending distally from the outer body portion, the first jaw member defining a hole configured for detachable receipt of a curved needle; and
    a second jaw member coupled to a distal end portion of the shaft and defining a hole configured for detachable receipt of the curved needle; and
    a first elongate locking element having a proximal end portion coupled to the first trigger, and a distal end portion, wherein the first elongate locking element is configured to move between a proximal, non-locking position in which the distal end portion of the first elongate locking element is disposed proximally of the hole of the first jaw member, and a distal, locking position in which the distal end portion of the first elongate locking element is disposed within the hole of the first jaw member for locking the curved needle to the first jaw member, wherein the first jaw member is configured to rotate with the outer body portion and relative to the second jaw member and the shaft about the longitudinal axis of the shaft.

14. The surgical suturing instrument according to claim 13, wherein the first jaw member defines a longitudinally-extending groove in communication with the hole of the first jaw member, the distal end portion of the first elongate locking element slidably disposed in the groove.

15. The surgical suturing instrument according to claim 13, further comprising a second elongate locking element having a distal end portion slidably received in the second jaw member, wherein the second elongate locking element is configured to move between:
    a proximal, non-locking position in which the distal end portion of the second elongate locking element is disposed proximally of the hole of the second jaw member for releasing the curved needle; and a distal, locking position in which the distal end portion of the second elongate locking element is disposed within the hole of the second jaw member for locking the curved needle to the second jaw member.

16. The surgical suturing instrument according to claim 13, further comprising a curved needle, wherein the curved needle has a first end defining a first notch configured for receiving the distal end portion of the first elongate locking element when the first end is in the hole of the first jaw member.

17. The surgical suturing instrument according to claim 16, wherein the curved needle has a second end defining a second notch.

18. The surgical suturing instrument according to claim 13, further comprising:

a push rod having a proximal end portion coupled to the first trigger and configured to translate in response to an actuation of the first trigger; and a bearing assembly disposed within the shaft and including:

an outer race; and an inner race supported in the outer race, wherein the proximal end portion of the first elongate locking element is coupled to the outer race or the inner race and a distal end portion of the push rod is coupled to the other of the outer race or the inner race for moving the bearing assembly and the first elongate locking element between the proximal and distal positions.

19. The surgical suturing instrument according to claim 13, wherein the end effector includes an inner body portion disposed within the outer body portion and rotationally fixed relative to the shaft, the second jaw member coupled to a distal end portion of the inner body portion.

20. The surgical suturing instrument according to claim 19, further comprising an actuation bar operably coupled to a second trigger of the handle assembly and configured to translate within the shaft in response to an actuation of the second trigger, wherein the outer body portion defines a cam slot having a portion of the actuation bar received therein such that translation of the actuation bar rotates the outer body portion and the first jaw member relative to the inner body portion and the second jaw member.

\* \* \* \* \*